United States Patent [19]
Gillespie et al.

[11] Patent Number: 5,265,840
[45] Date of Patent: Nov. 30, 1993

[54] PINCH VALVE

[75] Inventors: Lionel Gillespie, Atlanta; Joe Kopp, Decatur, both of Ga.; Matthew S. Solar, Cooper City, Fla.

[73] Assignee: Symbiosis Corporation, Miami, Fla.

[21] Appl. No.: 959,277

[22] Filed: Oct. 9, 1992

[51] Int. Cl.⁵ .................................................. F16K 7/00
[52] U.S. Cl. ............................................. 251/4; 251/7
[58] Field of Search ............................................. 251/7

[56] References Cited

U.S. PATENT DOCUMENTS

| | | |
|---|---|---|
| 1,675,231 | 6/1928 | Stoke . |
| 1,843,169 | 2/1932 | McKesson . |
| 2,237,014 | 4/1941 | Stoehrer ............................ 255/12 |
| 2,485,842 | 10/1949 | Pennington ...................... 128/214 |
| 2,615,668 | 10/1952 | Ernest .................................. 251/7 |
| 2,627,388 | 2/1953 | Johnson et al. ................... 251/118 |
| 2,876,937 | 3/1959 | Wilson ............................. 251/7 X |
| 3,044,466 | 7/1962 | Henderson ...................... 251/7 X |
| 3,157,201 | 11/1964 | Littmann ...................... 137/625.47 |
| 3,276,472 | 10/1966 | Jinkens et al. ................... 137/556 |
| 3,765,420 | 10/1973 | Felczak ............................ 128/347 |
| 3,830,225 | 8/1974 | Shinnick .......................... 128/2 B |
| 3,834,372 | 9/1974 | Turney ............................ 128/2 F |
| 4,106,508 | 8/1978 | Berlin ............................. 251/7 X |
| 4,451,257 | 5/1984 | Atchley ............................ 604/119 |
| 4,457,699 | 7/1984 | Hattori ........................... 251/7 X |
| 4,566,480 | 1/1986 | Parham ........................... 137/271 |
| 4,662,871 | 5/1987 | Rafelson .......................... 604/119 |
| 4,668,215 | 5/1987 | Allgood ............................ 604/30 |
| 4,776,840 | 10/1988 | Freitas et al. ..................... 604/33 |
| 4,881,523 | 11/1989 | Heckele ............................. 128/4 |
| 5,061,180 | 10/1991 | Wisle ................................ 433/91 |

Primary Examiner—John C. Fox
Attorney, Agent, or Firm—David P. Gordon

[57] ABSTRACT

A pinch valve for a flexible conduit is provided. The pinch valve has an arcuate rigid hook, an arcuate rigid pincher, and an actuator. The arcuate rigid hook has an inner surface of a diameter substantially equal to outer diameter of the flexible conduit, wherein the inner surface receives the conduit. The arcuate rigid pincher has an outer arcuate surface with a diameter at least as small as the inner diameter of the flexible conduit, and the flexible conduit is located between the arcuate hook and the arcuate rigid pincher. The actuator is coupled to either the hook or the pincher, and moves the hook relative to the pincher relative from a first position to collapse and pinch the flexible conduit therebetween to a second position where said flexible conduit is not collapsed and pinched. Preferably, the actuator is spring loaded so that the conduit is pinched. By providing the flexible conduit with a thick wall, the actuator may be actuated a small distance without permitting fluid flow through the flexible conduit. The pinch valve finds particular use in an endoscopic suction/irrigation instrument.

18 Claims, 18 Drawing Sheets

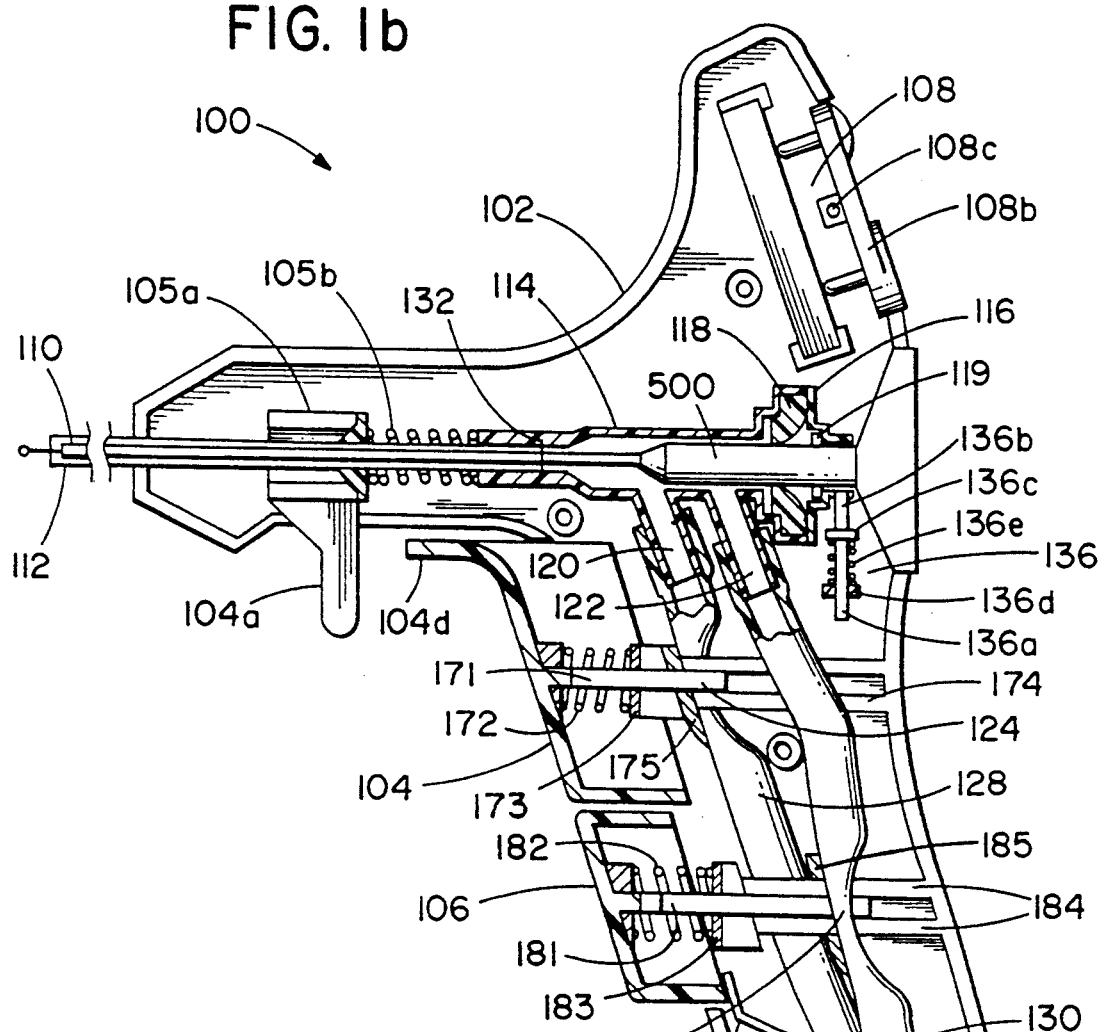
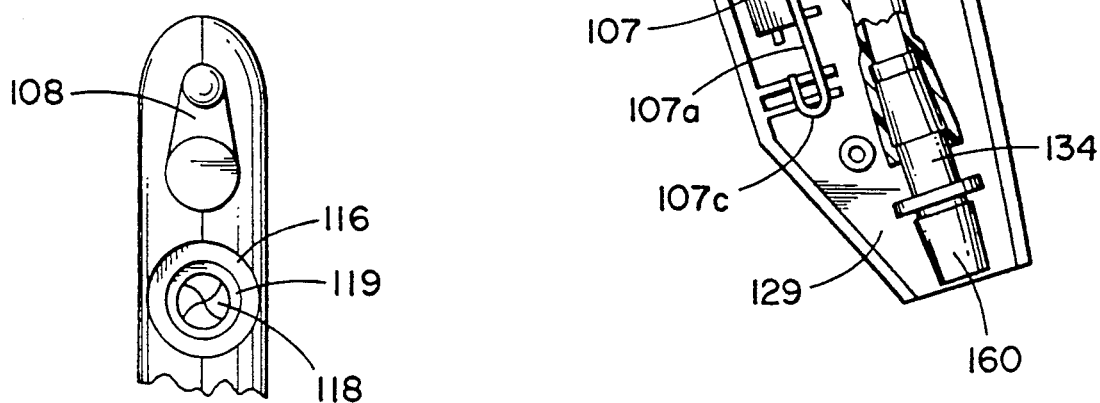

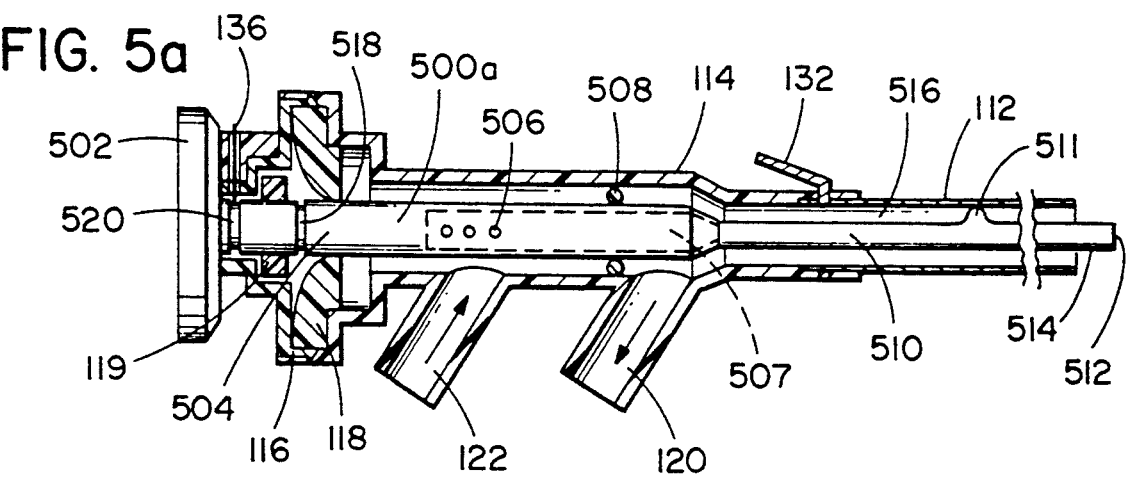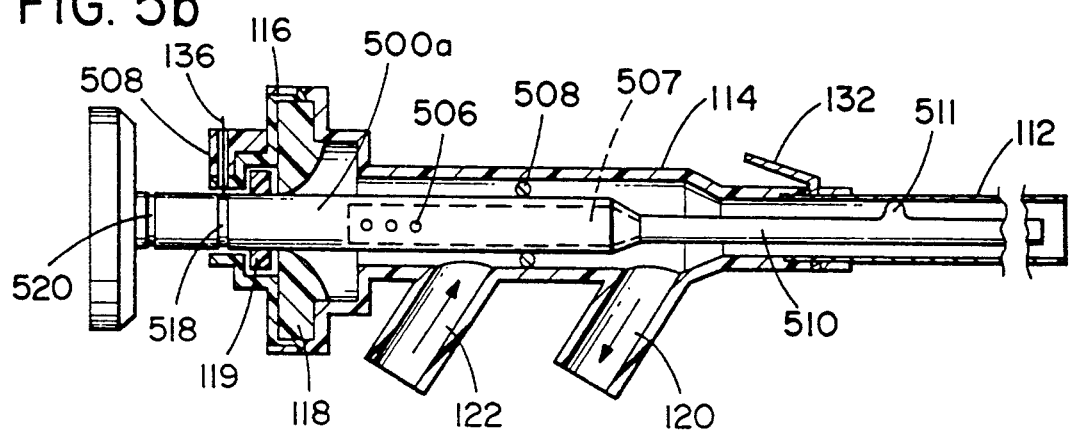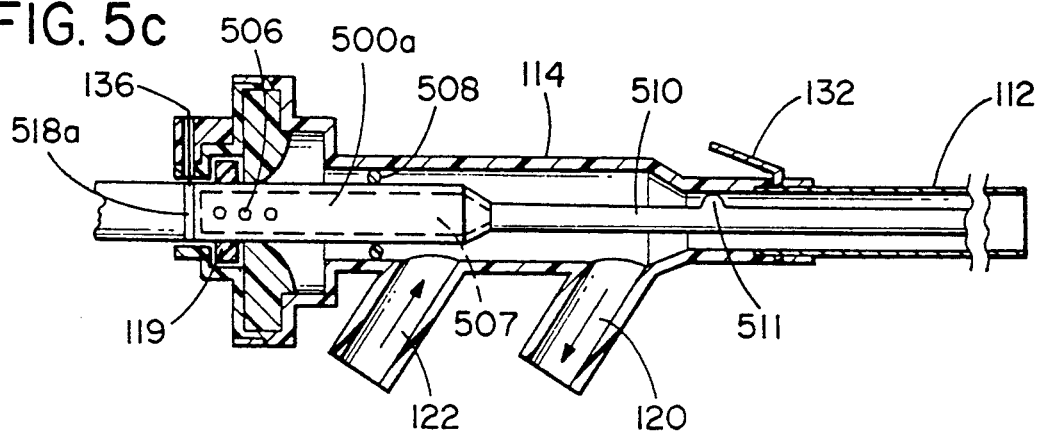

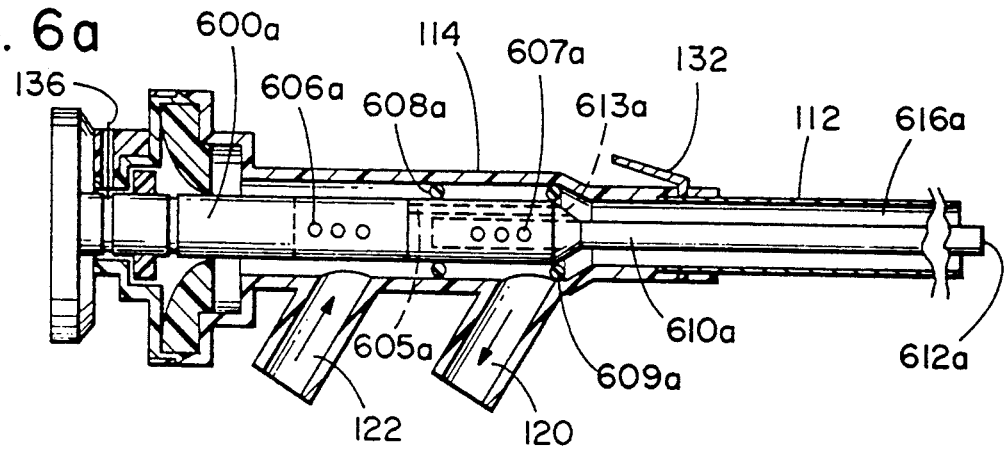
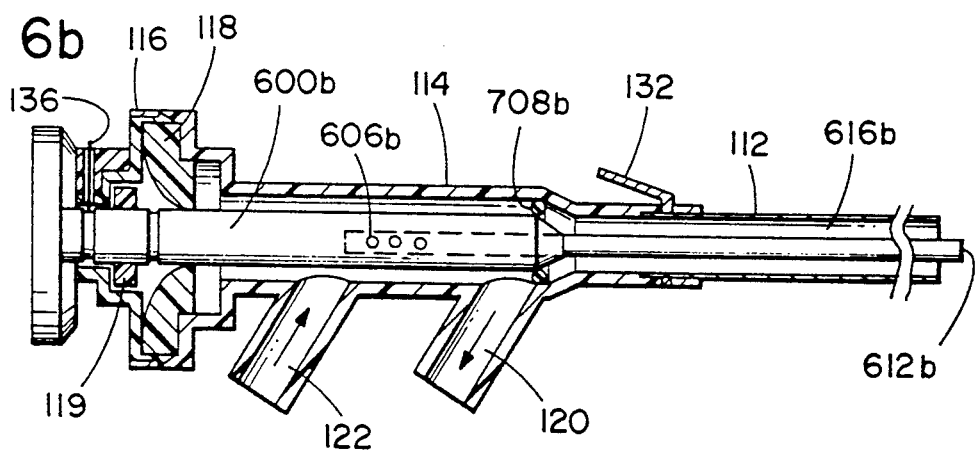
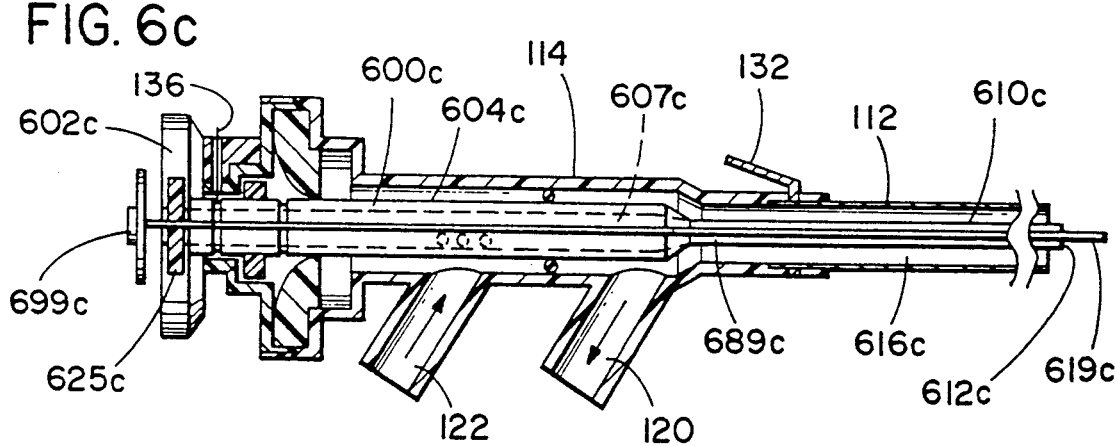

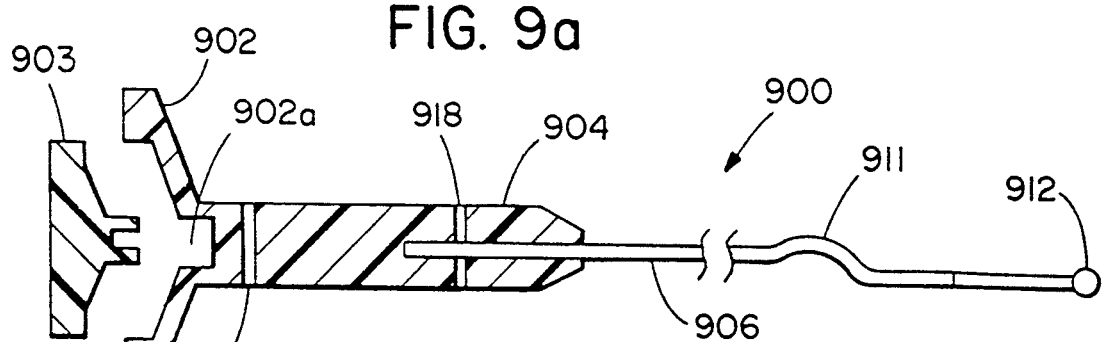
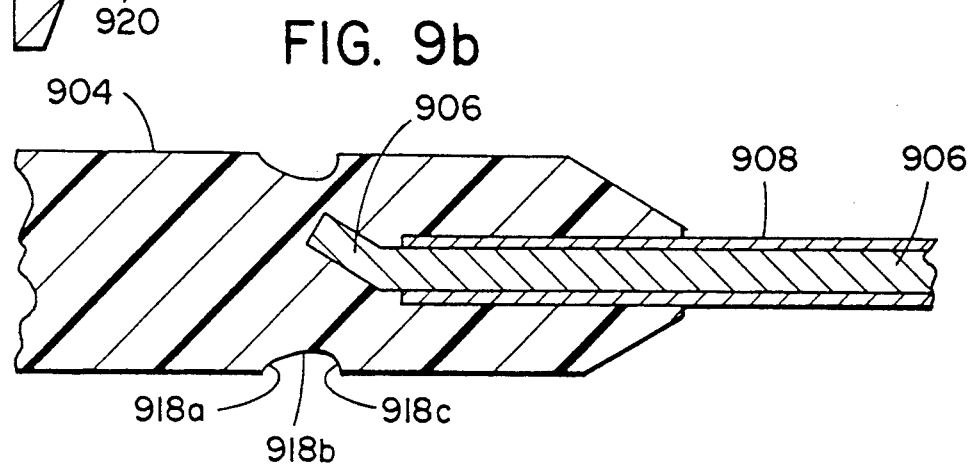
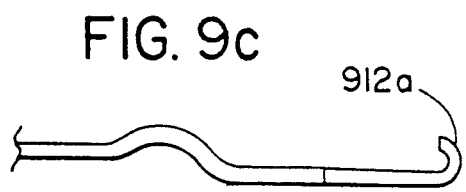 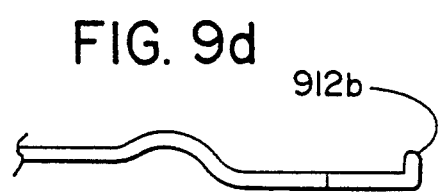
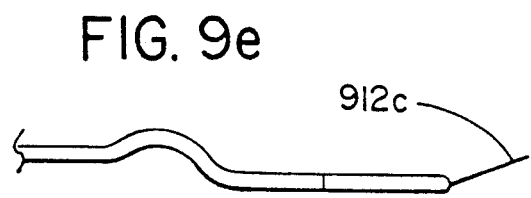 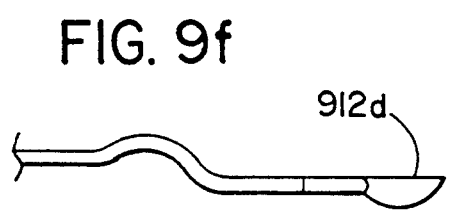
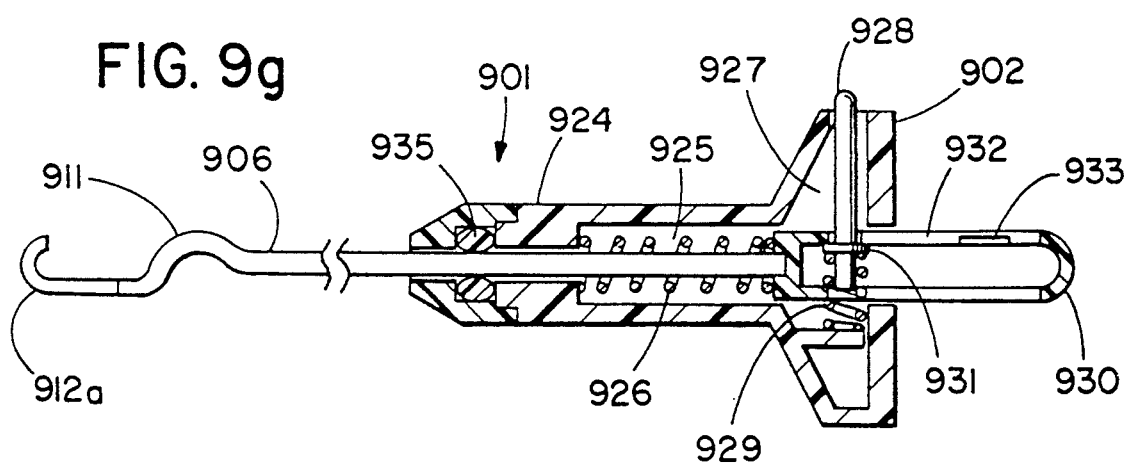

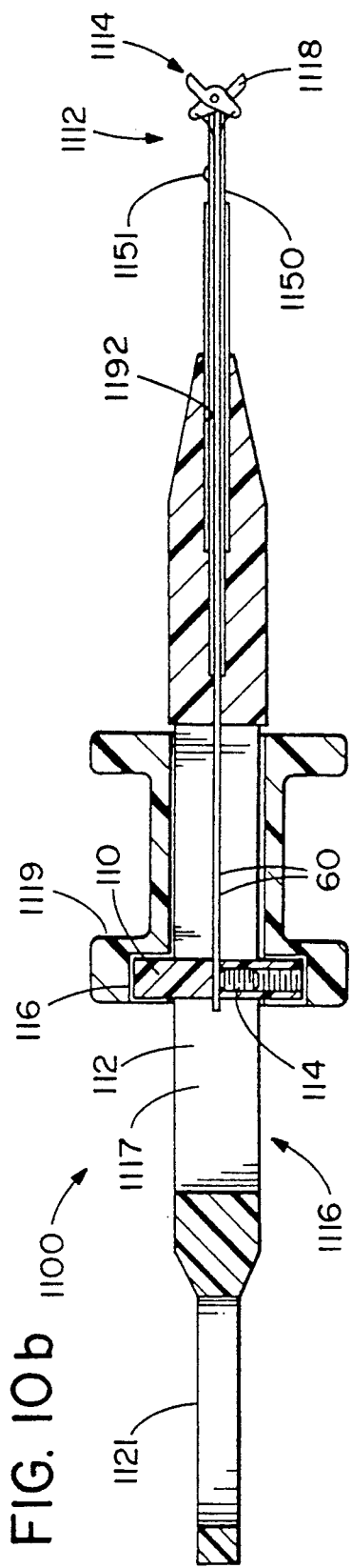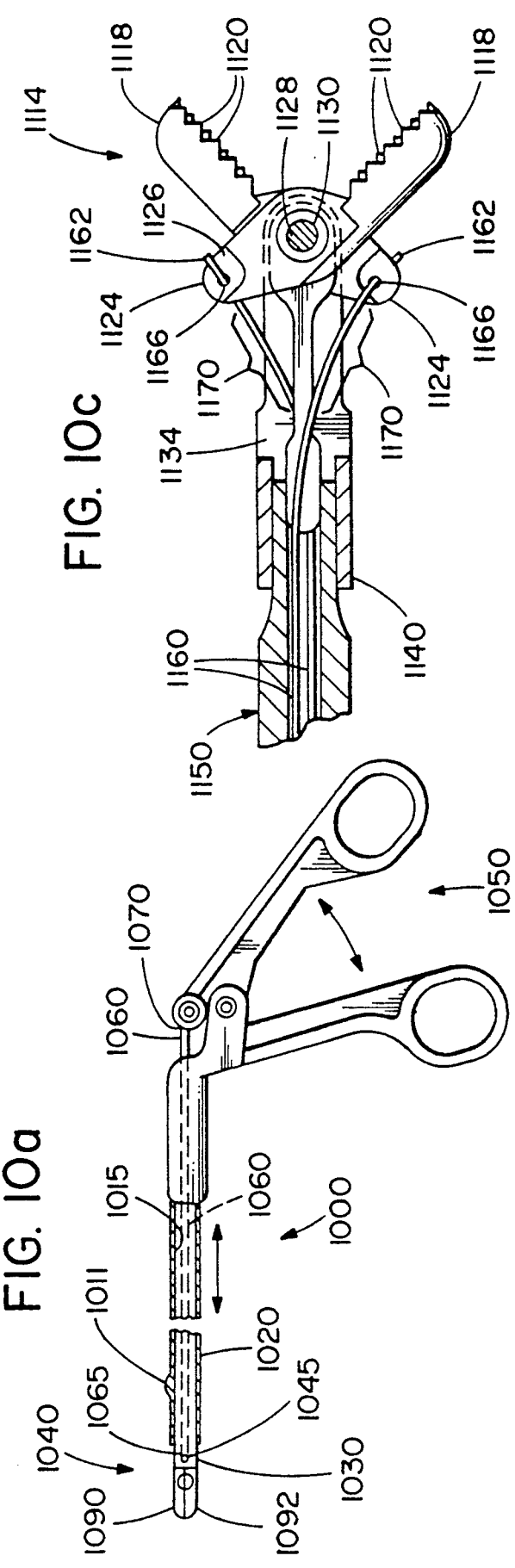
FIG. 10b
FIG. 10c
FIG. 10a

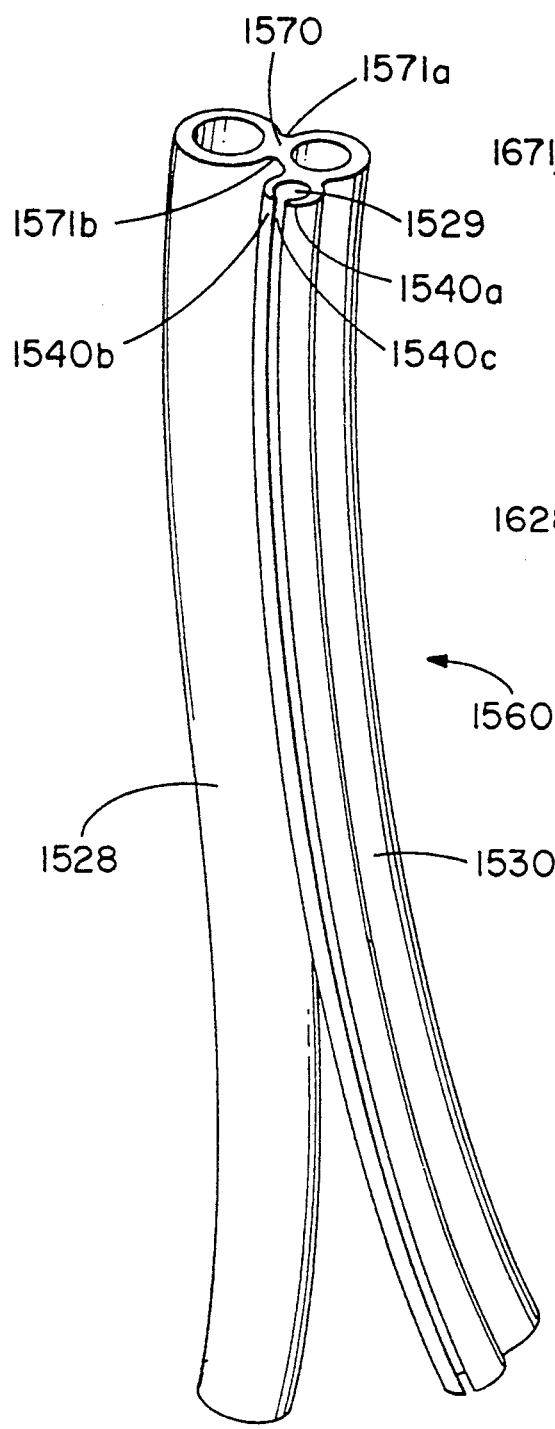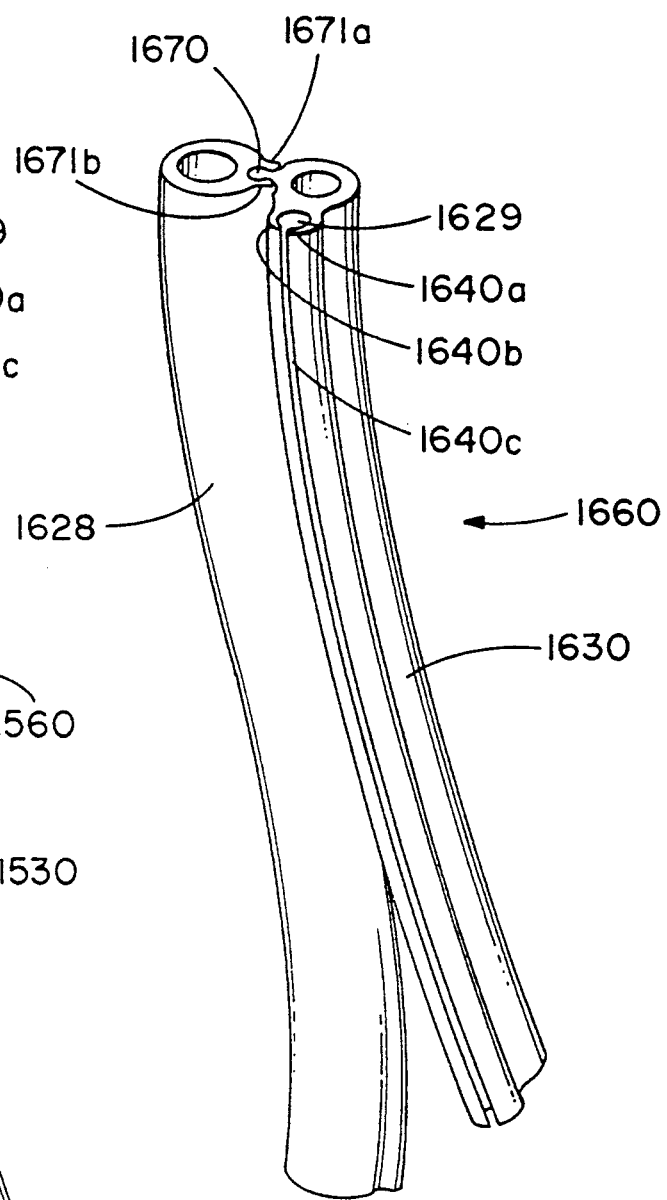

PINCH VALVE

BACKGROUND OF THE INVENTION

This invention broadly relates to endoscopic instruments. More particularly, this invention relates to a multifunction endoscopic instrument including suction, irrigation and electrocautery means.

Tools having both suction and irrigation features are well known in the art. Perhaps the earliest combination tool of this type is shown in U.S. Pat. No. 1,114,268 to Kells which discloses a "Method For Surgically Cleansing Wounds And Other Surfaces" where an irrigation tube enters a suction tube and the suction tube is covered with gauze or a swab. Irrigation fluid wets the gauze or swab and is sucked back by the suction tube. Rubber hoses may be grasped to control flow. Variations on this type of device include one shown in U.S. Pat. No. 3,810,471 to Truhan which discloses a "Surgical Aspirating Cannula". This is a combined irrigation-suction device where the suction tube is located within and is coaxial with the irrigation tube, and irrigation fluid is delivered in the annular space between the tubes. The distal end of the outer irrigation tube is sealed to the inner suction tube and the irrigation tube is provided with lateral openings. Even more recently, additional features have been added to combined suction-irrigation tools. U.S. Pat. No. 4,617,013 to Betz discloses a "Method and Apparatus For Surgical Irrigation, Aspiration and Illumination" having coaxial fiber optic, aspiration and irrigation tubes.

Tools combining suction and cautery features are also well in the art and an early tool of this type is shown in U.S. Pat. No. 2,888,928 to Seiger which discloses a "Coagulating Surgical Instrument" where combined cauterizing and suction is provided by a hollow tube cautery probe to which a suction tube is attached. The cauterizing tip is conical with a small opening at the apex of the cone and several lateral openings spaced down from the apex. More recent improvements in this type of tool are shown in U.S. Pat. No. 4,307,720 to Weber which discloses an "Electrocautery Apparatus and Method and Means for Cleaning the Same". This is a combination cautery-suction device where electrode and vacuum tubes are arranged parallel to each other in the same "wand". The electrode is retractable into the wand and retraction of the electrode scrapes the surface of the electrode to clean it. Other variations of this type of tool include yet other features. U.S. Pat. No. 4,207,874 to Choy discloses a "Laser Tunneling Device" which is a probe for a tube such as a blood vessel. The probe includes central fiber optics for illumination, viewing, and laser output surrounded by a coaxial tube with a switchable valve for aspiration or irrigation.

More recently, suction, irrigation, and cautery have been combined in the same tool. U.S. Pat. No. 4,886,491 to Parisi et al discloses a "Liposuction Procedure with Ultrasonic Probe" which includes ultrasonic cautery, suction and irrigation in the same probe.

While many of the tools of the prior art served a purpose at the time they were invented, they are generally inapplicable in today's modern endoscopic surgical procedures. An endoscopic procedure typically involves the use of trocars for making one or more small incisions in the abdomen or chest cavity. Trocar tubes are then left in place in the abdomen or chest cavity so that optical tools may be inserted therethrough for viewing and endoscopic surgical tools may be inserted therethrough for operating. A camera or magnifying lens optical tool is often inserted through the largest diameter trocar tube (e.g. 10 mm diameter) while a cutter, dissector, or other surgical instrument is inserted through a similarly sized or smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in another trocar tube.

Those skilled in the art will appreciate that endoscopy is a rapidly growing field of surgery because it is less invasive than classical surgery. However, it will also be appreciated that even with endoscopic surgery where the incisions are typically small, it is advantageous to limit the number of incisions made. The number of incisions must be balanced against the desirability of having several tools inserted and available simultaneously to the surgeon. Likewise, while it is possible to remove endoscopic tools and insert different tools during a procedure, it will be appreciated that repeated insertion and removal of different endoscopic tools through the trocar tubes is preferably avoided, as it can be difficult to locate the new tool at a desired location, and each insertion of a tool increases the risk of unnecessary trauma to the surgical site area.

Some attempts have been made to provide multifunctional endoscopic tools so that the number of incisions may be minimized while at the same time providing the physician with several tools available simultaneously. For example, U.S. Pat. No. 708,136 to Saito discloses a "Cautery Hemostatic Unit" which is deliverable through an endoscope and includes an irrigation nozzle. Other combination endoscopic tools are known and generally include combination suction-irrigation and suctioncautery probes. All of these probes occupy a trocar tube when in use and no other tools may be inserted in the trocar when occupied by one of these probes. Additional combinational tools and prototypes recently introduced include tools which have a plurality of different distal end portions which can be attached and removed from a single handle as desired to accomplish different functions. However, this arrangement requires repeated insertion and removal of the endoscopic tool through the trocar tube to the surgical site.

SUMMARY OF THE INVENTION

It is therefore an object of the invention to provide a multifunction endoscopic instrument which includes suction and irrigation functions.

It is a further object of the invention to provide a suction/irrigation endoscopic instrument where a cautery probe is inserted through the fluid chamber of the instrument.

It is another object of the invention to provide an endoscopic suction/irrigation/cautery instrument which permits the insertion of an additional endoscopic tool through the instrument.

It is also an object of the invention to provide a multifunctional endoscopic instrument having an ergonomic hand piece whereby suction, irrigation and cautery functions are easily controlled.

It is an additional object of the invention to provide an endoscopic instrument having a progressive suction control so that the amount of suction is easily adjustable.

A further object of the invention is to provide an endoscopic suction/irrigation/cautery instrument where the cautery is selectable between cutting and coagulating cautery voltages.

Another object of the invention is to provide a suction/irrigation endoscopic instrument where a distal end probe may be provided in a desired rotational position by insertion of the probe through the instrument and rotation thereof while the instrument stays in place.

An additional object of the invention is to provide a cautery/irrigation safety override mechanism which prevents the application of cautery during an irrigation procedure and thereby protects a patient from burns or shocks resulting from simultaneous irrigation and cautery functions.

Yet another object of the invention is to provide a multifunction endoscopic instrument which includes suction, irrigation, and a removable cautery probe where the cautery probe is lockable in one or more positions within the instrument.

Even a further object of the invention is to provide improved non-leak valves for suction/irrigation endoscopic instruments.

Another object of the invention to provide a T-ball valve for irrigation system having two fluid sources, where the T-ball valve permits the flow of fluid from either fluid source but automatically prevents backflow from one source to the other.

A further object of the invention is to provide a number of different types of probes which can be inserted into an endoscopic instrument so that suction, irrigation, cautery and selectable other functions are available to the physician through a single trocar tube.

An additional object of the invention is to provide a wellbuilt, relatively inexpensive disposable suction/irrigation/cautery endoscopic instrument.

Another object of the invention is to provide an improved molded two passage suction/irrigation conduit with means for carrying a cautery wire therebetween for the purpose of eliminating cable and conduit tangling.

Another object of the invention is to provide a suction/irrigation endoscopic instrument having tubing already attached to the instrument, and tubing connectors for easy attachment to tubing which extends from suction and irrigation sources.

It is even an additional object of the invention to provide a suction/irrigation endoscopic instrument having an outer sleeve providing a soft distal tip having cleanable side ports.

In accord with the objects of the invention, an endoscopic instrument having both suction and irrigation functions is provided and generally comprises a fluid chamber, a cannula in fluid communication with the distal end of a fluid chamber, a slit valve and an elastomeric gasket in the proximal end of the fluid chamber, irrigation and suction conduits communicating with the fluid chamber between the slit valve and the distal end of the fluid chamber, and valves for selectively opening and shutting off the irrigation and suction conduits. The fluid chamber, slit valve, and the irrigation and suction conduits are located in a pistol shaped shell, and triggers are utilized to actuate the valves which open and shut off the irrigation and suction conduits. Also located inside the shell is an electrical circuit with an electrical contact which contacts a metal portion of the cannula over which an insulating sleeve is provided and which supplies a cauterizing voltage thereto. Different cautery probes are provided. The cautery probes are inserted through the slit valve in the proximal end of the instrument and each cautery probe includes an uninsulated portion which is formed to contact the metal cannula and obtain the cautery voltage therefrom.

There are many preferred aspects of the invention which provide advantageous features. One preferred aspect includes means for regulating the amount of suction through the cannula. The regulating means includes providing the insulating sliding sleeve which covers the cannula with a plurality of longitudinally spaced distal lateral openings, and means for sliding the insulating sleeve relative to the cannula in order to incrementally close the off the lateral openings. Several different mechanisms for causing the sleeve to slide are provided. Another preferred aspect of the invention is a safety cautery/irrigation override mechanism. The override mechanism includes an electrical switch in the irrigation trigger which overrides the supply of cautery voltage to the electrical contact so that no cautery is possible while irrigating. Another safety feature relating to the cautery procedure is a probe arrangement which prevents shocks to the physician. The probe arrangement comprises insulation which shields the probe along its entire length up to the cauterizing distal end except for a segment which contacts the cannula for electrical contact.

With the slit valve and elastomeric sealing gasket at the proximal end of the fluid chamber, fluid is prevented from exiting the proximal end of the chamber but probes or other instruments may be inserted therethrough. For example, besides the cautery probes, irrigation-hydrodissection, injection- aspiration probes, and other probes are provided. One probe includes a tube with lateral holes in communication with the fluid chamber at the irrigation conduit, and an O-ring on the probe for contacting the fluid chamber between the irrigation conduit and suction conduit openings. In this manner irrigation is directed through the probe which extends through the cannula, and at the same time, suction is directed through the cannula and around the probe. If the distal end of the probe is made very small in diameter, the probe may be used for hydrodissection. Many different probes for accomplishing different functions are also provided. All of these probes are inserted through the slit valve in the proximal end of the instrument. The handles of all of the different probes are preferably provided with color coded inserts so that the probe can be identified as to type while it is located within the suction/irrigation instrument.

Besides the ability to insert probes through the slit valve, endoscopic and laparoscopic type instruments with end effectors for grasping, cutting, dissecting, biopsy sampling, etc. may also be inserted therethrough and through the fluid chamber. These instruments may be particularly arranged to include an uninsulated cautery pickup, so that the end effectors can be used for cautery purposes. With the ability to insert such instruments through the slit valve, surgical methods are provided which do not require separate incisions and trocar tubes for suction/irrigation, cautery, and manipulation.

Additional preferred aspects of the invention include: a pinch valve arrangement for the suction and irrigation conduits, including a semicircular hook for collapsing and pinching the conduit against a semicircular protrusion; a pistol shaped shell provided with a rocker thumb switch which controls the selective application of cutting and coagulating voltages to the electrical cautery contact; a special molded "spinal cord" tubing having suction and irrigation conduits which together define a rib indenture into which a cautery wire is snapped so that the the suction and irrigation tubes and cautery wire exiting the suction/irrigation instrument are easily managed; probes with grooves which interact with a locking pin provided in the shell so that probes may be held in an inactive position in the fluid chamber; and a T-ball valve for regulating the irrigation from two fluid sources, where the T-ball valve permits the flow of fluid from either fluid source but automatically prevents backflow from one source to the other. In addition, other embodiments of aspects of the invention are provided, including a fluid chamber with only a single inlet for suction and irrigation, and a trigger mechanism utilizing poppet valves in place of pinch valves to control suction and irrigation.

Additional objects and advantages of the invention will become apparent to those skilled in the art upon reference to the detailed description taken in conjunction with the provided figures.

BRIEF DESCRIPTION OF THE DRAWINGS

FIG. 1b is a side view of the instrument of FIG. 1a with one half of the instrument shell removed.

FIG. 1c is a detail of an indicated portion of FIG. 1a showing the slit valve and the thumb rocker cautery/coagulation switch.

FIGS. 4a and 4b are respectively a side cross sectional view and a top cross sectional view of a preferred fluid chamber for the instrument of FIG. 1a.

FIGS. 5a and 5b are cross sectional views of the preferred fluid chamber of the invention with a probe partially and fully inserted therein.

FIG. 5c is a cross sectional view of an alternative probe partially inserted into the fluid chamber of the invention.

FIGS. 6a, 6b, 6c, and 6d are views similar to FIGS. 5a, but showing different kinds of probes for effecting suction and irrigation in different manners.

FIGS. 8d–8g show views of a preferred cautery override switch and circuit board used in the electrical circuit of FIG. 8a.

FIGS. 8h–8k show views of a preferred cut/coagulation cautery switch and circuit board used in the electrical circuit of FIG. 8a.

FIG. 9a is a partially exploded cross-sectional view of a first cautery probe.

FIG. 9b is an enlarged view of a portion of of the probe of FIG. 9a.

FIGS. 9c–9f show the distal ends of different types of cautery probes.

FIG. 9g is a cross-sectional through another embodiment of a probe with a mechanism for permitting the probe to be extended out of the cannula and to be withdrawn into the cannula.

FIG. 10a is a schematic views of an endoscopic tool which can be inserted through the suction/irrigation instrument of FIG. 1a.

FIGS. 10b and 10c are respectively a side view in partial cross section, and an enlarged view of the distal end the endoscopic biopsy forceps tool of FIG. 10b which can inserted through the suction/irrigation instrument of FIG. 1a.

FIGS. 11g and 11h are perspective views of third and fourth embodiments of the molded tubes having suction and irrigation conduits and a rib indenture for holding a cautery wire.

DETAILED DESCRIPTION OF THE PREFERRED EMBODIMENTS

Figure 1A:
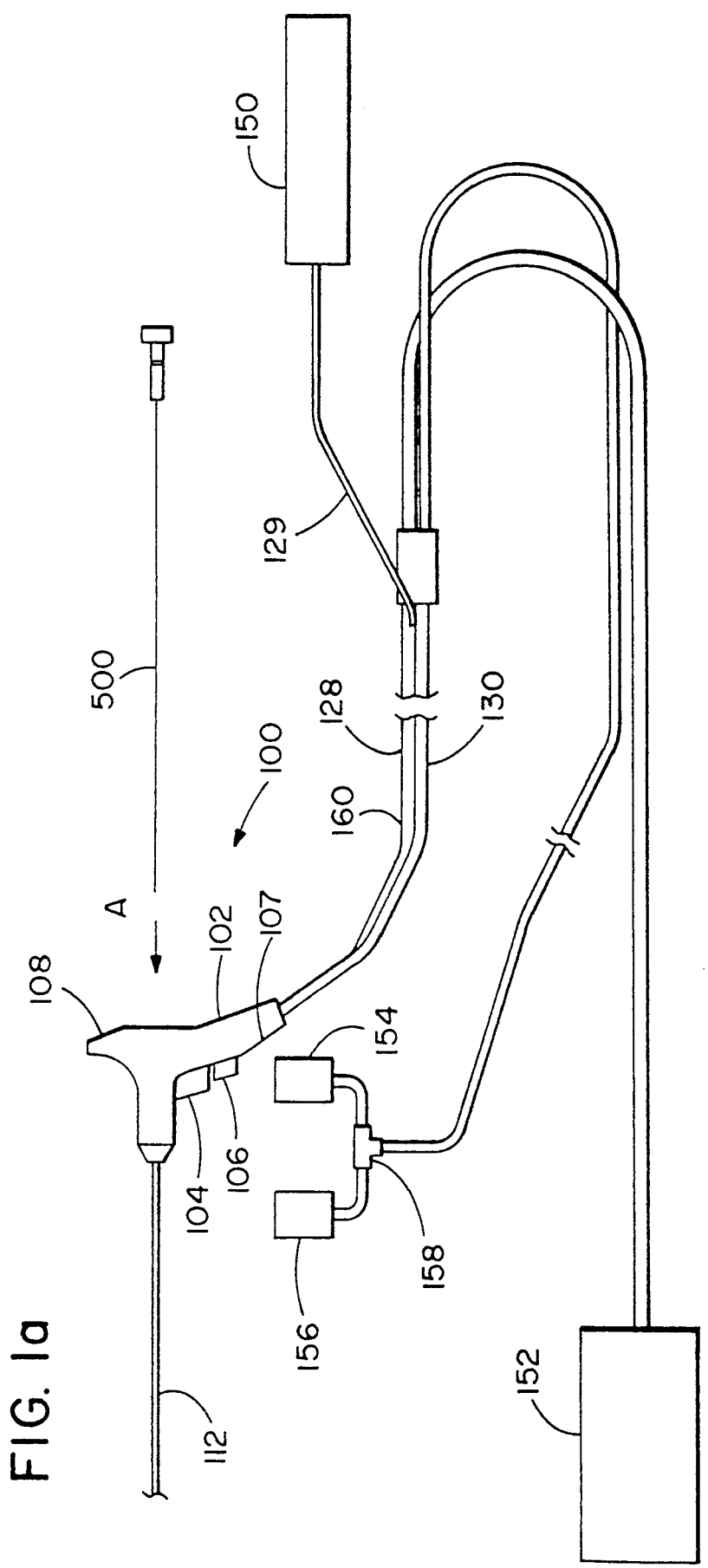
FIG. 1a is a perspective view of the suction/irrigation instrument of the invention showing the fluid and electrical connections of the instrument with other portions of the invention as well as a cautery probe for insertion into the instrument.

Referring now to FIGS. 1a and 1c, the endoscopic electrosurgical suction-irrigation instrument 100 of the invention is shown having a pistol-shaped shell 102, suction and irrigation trigger switches 104 and 106, irrigation/cautery override switch 107, cautery cut/-coag rocker switch 108, and cannula 112. The instrument 100 is connected to an electrical source 150, a vacuum source 152 and an irrigation fluid source 154 or sources 154, 156. A probe 500, such as an electrosurgical (cautery) probe or the like is shown located outside of the instrument 100, but intended for insertion by movement as indicated by arrow "A" into and through the instrument.

Figure 4B:
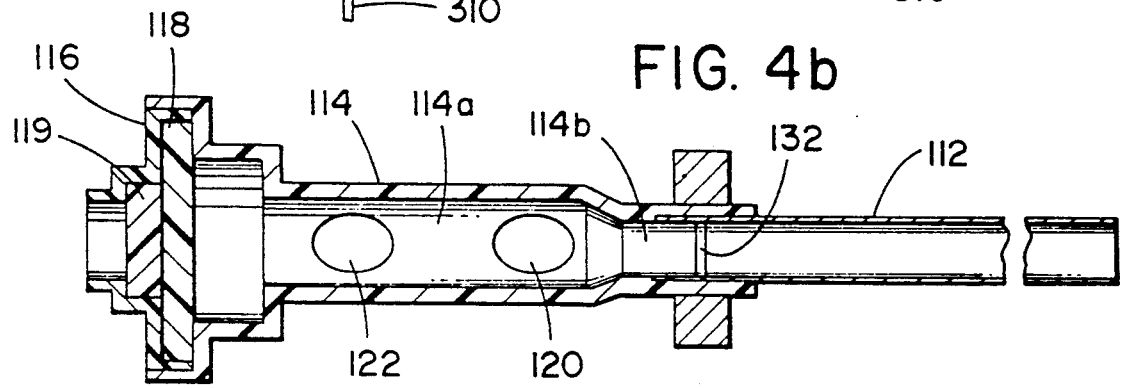
Figure 4A:
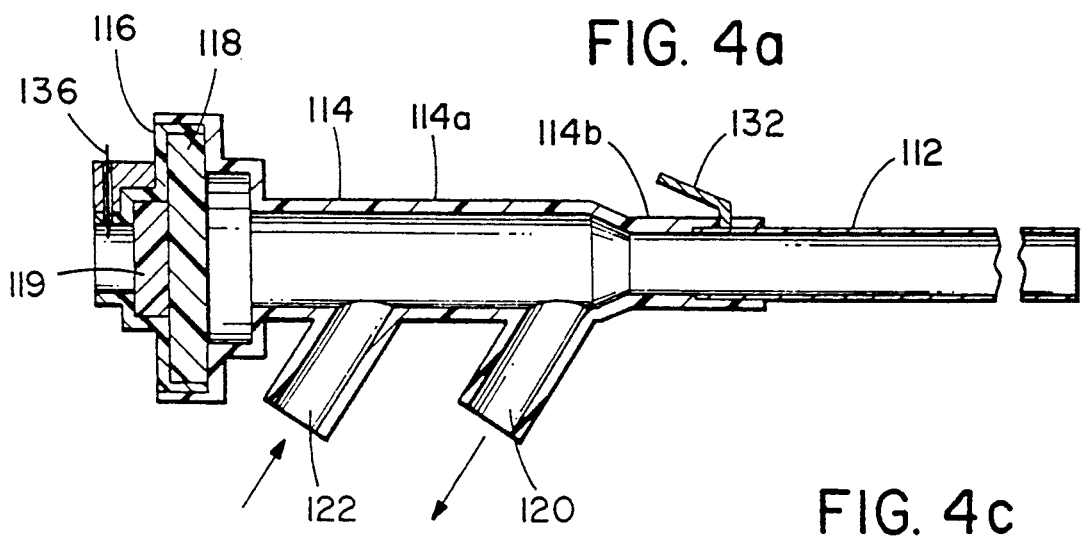

In the preferred embodiment of the invention, within the pistol shaped shell 102 of the instrument 100 is a fluid chamber 114 (seen in FIGS. 1b, 4a and 4b). The cannula 112 is held in the chamber 114 and extends distally there from. The proximal end of the fluid chamber is sealed by a slit-valve 118 or the like as described hereinafter. Thus, for effecting cautery or other functions hereafter described, the probe 500 is inserted through the slit valve 118 and into and through the fluid chamber 114.

With the provided suction-irrigation instrument 100, suction and irrigation are controlled by trigger switches 104, 106, and cauterization is controlled by thumb switch 108 or by foot switches (not shown) as hereinafter described. Irrigation trigger switch 106 is provided with an electrical safety override 107 switch which disables the thumb switch 108 when irrigating. The shell 102 receives a suction vacuum tube 128, an electrical supply wire 129, and an irrigation supply tube 130 via a "spinal cord" molded tubing 160 which is discussed in detail below with reference to FIGS. 11a–11d. Two sources of irrigation fluid 154, 156 may be selectively supplied to the instrument 100 by using a T-ball valve 158 which is also discussed in detail below with reference to FIGS. 12a–12e.

Turning now to FIG. 1b, the shell 102 can be seen with trigger switches 104 for suction and 106 for irrigation and a double action or rocker thumb switch 108 for electrosurgical cutting and coagulation (also shown in detail in FIG. 1c). The distal end of the body 102 is provided with an appropriately sized metal cannula 112 (typically 5 mm or 10 mm) which is covered by an insulating sliding sleeve 110 (described in detail below). The proximal end of the cannula 112 communicates with the distal end of the fluid chamber 114 which is housed within the shell 102. The fluid chamber 114 terminates at the proximal end of the shell 102 with a slit valve 118 and elastomeric sealing gasket 119. The slit valve 118 and sealing gasket 119 permit probes of different types including electrocautery probes which are discussed in detail below to be inserted into and through the fluid chamber 114 while still preventing fluid leakage out the distal end of the instrument. More particularly, the slit valve 118 prevents leakage when no probe or tool is inserted therethrough, while the sealing gasket 119 (and to some extent the slit valve) prevents leakage when a probe or tool is inserted through the proximal end of the instrument 100.

As seen in FIG. 1b, in communication with the fluid chamber 114 are the suction conduit or tube 128 (via suction port 120) and the irrigation conduit or tube 130 (via irrigation port 122). The suction conduit 128 extends through a pinch valve mechanism 124 and is coupled through a tubing junction connector 134 near the base of the shell 102 to the suction portion of the spinal cord tubing 160, and thence to Vacuum supply 152 (FIG. 1a). The suction valve 124 is operated by trigger switch 104. As discussed below with reference to FIGS. 7a and 7b, the suction trigger switch 104 may be divided into two switches 104a and 104/104d for controlling normal suction and "super suction". The irrigation conduit 130 similarly extends through an irrigation valve mechanism 126 and is coupled through tubing junction connector 134 to the irrigation portion of the spinal cord tubing 160, and thence to irrigation supply 154 (156). The irrigation valve is operated by trigger switch 106.

Figure 3A:
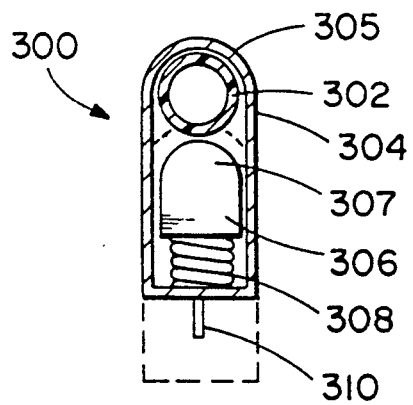
FIGS. 3a and 3b are details of the preferred pinch valve of the invention, showing the pinch valve causing a conduit to be in respectively open and closed positions.
Figure 3B:
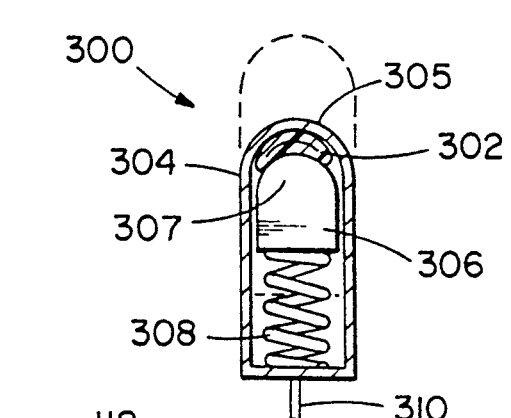

The suction valve 124 and irrigation valve 126 seen in FIG. 1b are standard type pinch valves, although for larger (e.g., 10 mm) instruments, different pinch valves discussed below with reference to FIGS. 3a and 3b are preferred. The suction valve 124 is arranged with a stem 171, a spring 172, a spring seat 173, a guide 174, and a valve seat 175. The stem 171 is coupled to the trigger 104 and moves with the trigger. The spring sits in the trigger 104 and is seated on the spring seat 173 which is formed in the shell 102 of the instrument 100. Thus, as the trigger 104 is pressed, the trigger is acting against the force of the spring 172 which is being compressed against the spring seat 173. The stem 171 of the suction valve 124 is preferably formed as a thin rectangular plastic piece with a large slot (not shown) in the middle which effectively forms a rear hook. The plastic piece is set in the guide 174 formed in the shell 102. In FIG. 1b, the suction tube 128 is shown extending through the slot in the stem 171 with the rear hook pulling, squeezing, and pinching the tube 128 against the valve seat 175. Because the suction valve 124 is set forward of the irrigation valve, there is room for the irrigation tube 130 in the handle of the shell when the stem 171 is forced backward in guide 124 to open the suction tube 128. In other words, with the provided arrangement, the suction valve 124 does not interfere in any manner with the irrigation tube 130.

The irrigation valve 126 is similarly arranged to the suction valve, and includes a stem 181, a spring 182, a spring seat 183, a guide 184, and a valve seat 185. The stem 181 is coupled to the trigger 106 and moves with the trigger 106. The spring 182 sits in the trigger 106 and is seated on the spring seat 183 which is formed in the shell 102 of the instrument. As the trigger 106 is pressed, the trigger acts against the force of spring 182. The stem 181 of the irrigation valve 126 is also preferably formed as a thin rectangular plastic piece with a large slot (not shown) in the middle for forming a rear hook. Care is taken to make the slot large enough to accommodate the suction tube 128 which also extends through the slot and which must not be pinched when the irrigation valve 126 is actuated. In FIG. 1b, the irrigation tube 130 is shown with the rear hook of the stem 181 pinching the tube 130 against the valve seat 185. Pressing of the trigger 106 moves the stem 181 backwards and releases the tube 130 for irrigational flow.

An electrical contact 132 (shown in more detail in FIG. 4) is provided toward the distal end of the fluid chamber 114, for connection with an electrocautery probe as will be discussed in detail below. The electrical signal applied to the electrical contact 132 is controlled by double action switch 108 activated by a rocker mechanism 108b which rocks over pivot 108c as described hereinafter with reference to FIGS. 8h–8k. Other aspects of the instrument 100 seen in FIG. 1b include a probe locking mechanism 136 described hereinafter with reference to FIGS. 5a–c; a spring biased mechanism 105a, 105b for moving the insulating sheath 110 relative to cannula 112 in order to effect supersuction as described in more detail with reference to FIGS. 7a and 7b; a spring mechanism 107a, 107b for activating cautery override switch 107 as discussed in more detail with reference to FIGS. 8a–8d; and an end cap 116 for the fluid chamber as discussed hereinafter in more detail with reference to FIGS. 4a and 4b.

As shown in FIG. 1b, even without any probe(s) inserted, the instrument 100 is functional as a suction-irrigation tool. When inserted in the body of a patient, the cannula 112 with insulating sliding sleeve 110 delivers irrigation fluid when the irrigation trigger 106 is squeezed to open the normally closed irrigation valve 126, thereby coupling the irrigation fluid tube 130 with fluid chamber 114 and thus to cannula 112. Similarly, cannula 112 provides suction when trigger 104 is squeezed and the normally closed suction valve 124 opens to couple vacuum tube 128 with fluid chamber 114 and thus with cannula 112. If triggers 104 and 106 are squeezed simultaneously, the irrigation fluid can be used to clean out a portion of the fluid chamber 114 as well as the suction port 120 and suction tube 128.

Turning to FIGS. 3a and 3b, a preferred embodiment of a pinch valve 300 used as the suction and irrigation valves 124, 126 of FIG. 1b is seen in the activated open and normally closed positions. The pinch valve 300 of FIGS. 3a and 3b is used with a resilient conduit or tubing 302 (such as suction tube 128 or irrigation tube 130 of FIG. 1b) and is preferred because it virtually eliminates leakage. In the activated open position of FIG. 3a, flow through conduit 302 is permitted. In the default or normally closed position of FIG. 3b, no flow is permitted through conduit 302. As seen in FIGS. 3a and 3b, valve 300 comprises a hook member 304 having a curved inner surface portion 305 conforming to the outside diameter of resilient conduit 302, a fixed dome shaped stopping block 306 which has a similarly conforming but slightly smaller diameter curved portion 307, a spring 308, and an actuator 310. In the normally closed position of FIG. 3b (also shown in FIG. 1b) the hook 304 is biased by spring 308 to press inward against dome block 306, whereby the resilient conduit 302 is collapsed and pinched in a curved manner assuring a virtually complete stoppage of flow through the conduit 302. However, when the actuator 310 is squeezed against the force of spring 308, the hook 304 moves away from the dome block 306 (which is fixed in position), as the spring 308 is compressed. With the domed block 306 no longer squeezing the resilient conduit 302, the resilient conduit 302 resumes its normally round and open position as shown in FIG. 3a.

Those skilled in the art will appreciate that the actuator 310 of FIG. 3a is coupled to trigger switches 104, 106 discussed with reference to FIG. 1b. In addition, the preferred embodiment of pinch valve 300 is useful primarily when the tubes 302 are of sufficiently large diameter so as to readily collapse into an arcuate shape as suggested by FIG. 3b. With tubes of diameter, a standard pinch valve is best used since small tubes cannot readily be folded into the FIG. 3b configuration. In either case, however, it is desirable that the tubes 302 have a relatively thick resilient wall. In this manner, when suction trigger switch 106 is squeezed, the trigger will travel enough distance to activate safety override switch 107 before the valve 300 permits fluid to flow through the tube 302 (130 in FIG. 1b). In other words, the resilient tube should be thick enough so that the override switch 107 is activated while the tube is decompressing as opposed to the walls of the tube separating from each other. This feature will be discussed in more detail below in reference to FIGS. 8a–8d.

Details of the fluid chamber 114 of instrument 100 are seen with reference to FIGS. 4a and 4b. In the preferred embodiment of the invention, the suction conduit 120 is located downstream (distal) of the irrigation conduit 122, and the internal diameter of the fluid chamber 114 is larger in the vicinity of the suction and irrigation conduits (114a) than it is at 114b in the vicinity of the cannula 112. One purpose of providing a narrowing fluid chamber is to provide a seat against which the probes can stop. Another reason is to accommodate O-ring washers which form parts of some of the probes of the invention as will also be discussed in detail below. However, it should be appreciated that it is not necessary that the fluid chamber narrow in the way shown in FIGS. 4a and 4b, or that the suction conduit be located distal of the irrigation conduit. Indeed, the fluid chamber can be constructed of a constant diameter, and the conduits reversed.

As seen in FIGS. 4a and 4b, the proximal end of fluid chamber 114 is covered with an end cap 116 which houses a slit valve 118 and an elastomeric sealing gasket 119 as previously mentioned. The end cap 116 is formed to mate with the proximal end of the fluid chamber 114. The function of the end cap 116 is to permit the slit valve 118 and sealing gasket 119 to be inserted into the proximal end of the fluid chamber during assembly, and to be held there during use of the instrument. Also preferably located at or near the proximal end of the fluid chamber 114 or at the end cap 116 is a spring biased locking pin mechanism 136. Locking pin mechanism 136, as seen in more detail in FIG. 1b, preferably includes a pin 136a having an engaging end 136b, a circumferential flange extending around the pin 136c, a stop 136d extending from the shell 102, and a spring 136e which is loaded between the stop 136d and the flange 136c. As will be discussed in more detail hereinafter, the locking pin 136a is spring biased in a position toward the fluid chamber 114 and is used to releasingly mate with at least one detent on a probe so that the probe can be held in a retracted position within the fluid chamber 114.

Figure 4C:
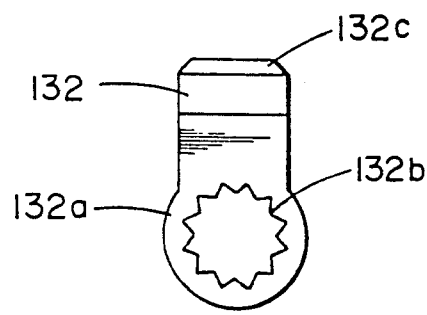
FIG. 4c is a detailed view of the cautery electrical contact coupled to the cannula in the fluid chamber of FIG. 4a and 4b.

Located toward the distal end of the fluid chamber is the electrical contact 132 which is shown in more detail in FIG. 4c. The electrical contact preferably comprises a washer 132a which is insert molded into the fluid chamber 114. The washer 132a has ridges 132b and a tab 132c. The ridges 132b are used to make electrical contact with the metal cannula 112, and the tab 132c is used for electrical connection to a wire coupled to a current source as discussed in more detail hereinafter with reference to FIGS. 8a–8c.

FIGS. 5a and 5b show a probe such as a hydrodissection probe 500a which is held in two different positions in fluid chamber 114. The hydrodissection probe 500a is provided with a closed end proximal handle portion 502 from which a shaft portion 504 extends. The shaft portion 504 is provided with lateral holes 506 and a longitudinal bore 507 extending from the holes 506 to the hollow rod 510 which extends through the cannula 112. The longitudinal bore 507 and the hollow rod 510 are in fluid communication. While the distal end of probe 500a may be configured in a number of ways as will be described in detail below with reference to FIGS. 9a-9f, in order to be a hydrodissection probe, the hollow rod 510 of probe 500a should be extremely narrow in cross-section and should have a distal opening 512 at the tip of the hollow rod 510. Also, to enable the probe 500a to provide a cautery function, the hollow rod portion 510 is provided with an uninsulated bump 511 which contacts cannula 112 (when the probe is in the position shown in FIG. 5a), and a distal uninsulated cauterizing surface 514. In this manner, the uninsulated bump 511 makes electrical contact with the cannula 112 (which is provided with current via contact 132) and conducts the current to the distal cauterizing surface 514.

In accord with a preferred aspect of the invention, the probe 500 is also provided with one or more detents 518 and 520 into which engage probe locking pin 136 can engage. As shown in FIG. 5a, when the probe 500a is fully inserted into the fluid chamber 114 so that locking pin 136 engages detent or groove 520, the O-ring 508 aligns itself between the irrigation port 122 and the suction port 120. As shown in FIGS. 5a and 5b, the outer diameter of the hollow rod portion 510 of the probe is much smaller than the inner diameter of the cannula 112 with an annular space 516 being established therebetween. Thus, two fluid paths are established. In particular, the O-ring divides the fluid chamber 114 into two portions, with a first portion located between the slit valve 118 or gasket 119 in the end cap 116 and the O-ring 508, and the second portion located between the O-ring 508 and the cannula 112. The irrigation fluid supplied through irrigation port 122 is trapped between the slit valve and the O-ring in the first portion of fluid chamber 114 so that it is forced into lateral holes 506 where it is communicated through the interior of the shaft of the probe to the distal end opening 512. Suction applied through suction port 120 to the second portion of the fluid chamber 114, however, is directed by the O-ring to the annular space 516 between the smaller diameter portion 510 and cannula 112. Thus, suction and irrigation may be accomplished at the same time. Also, as the bump 511 on the hollow rod is contacting the metal cannula, cautery and suction may be accomplished at the same time. Irrigation and cautery, however, cannot be accomplished simultaneously due to the cautery/irrigation override arrangement discussed hereinafter with reference to FIGS. 8a-8c.

It will be appreciated that the probe 500a may be withdrawn to a second position shown in FIG. 5b where locking pin 136 engages detent 518. In this position, while a cautery connection is made between bump 511 and cannula 112, a cautery procedure cannot be carried out, as the distal end of the probe no longer extends through the distal end of cannula 112. However, because the detents are located close to each other, the O-ring 508 still separates the fluid chamber into two portions, and irrigation may continue through the hollow rod 510, and suction may continue through the annulus 516. In addition, since the probe is in place, it is readily available for use by pushing it forward to the position shown in FIG. 5a.

In FIG. 5c, a modified cautery probe is shown so that the front locking detent 518a is located substantially distal the rear detent (not shown in FIG. 5c). In this situation, when the cautery probe is pulled backward until locking pin 136 engages the detent 518a, the bump 511 on the probe does not contact the cannula, and cautery cannot be conducted because the probe no longer extends through the distal end of the cannula 112 and because no electrical contact is made. In addition, irrigation and suction cannot be accomplished at the same time, as the O-ring 508 no longer separates the fluid chamber into two portions. However, with this arrangement, if the suction and irrigation triggers are activated at the same time, as previously described, a cleaning of the fluid chamber can be effected.

Those skilled in the art will appreciate that if desired, the functions discussed above with reference to FIGS. 5b and 5c can be combined by providing the probe with both detents 518 and 518a, so that two stops are provided at different locations. Also, it will be appreciated that detent 520 is not necessarily provided, as the handle 502 can act as a stop for the fully inserted position.

While the locking pin mechanism of FIGS. 5a-5c is shown schematically, it will be appreciated that the locking pin mechanism 136 of FIG. 1b is preferred. With that arrangement, as the probe 500a is inserted into the fluid chamber, the hollow rod 510 will extend past the locking pin mechanism without touching it. However, as the shaft enters the end cap area, the taper on the distal end of the shaft will contact the locking pin 136a and the locking pin will ride up and along the shaft and into detent 518. The detent 518 and the end 136b of the locking pin 135a are preferably shaped and formed in certain manners as discussed hereinafter with reference to FIGS. 9a and 9b so that it is relatively easy to move the probe 500a forward so as to disengage the locking pin 136a from the detent 518 upon forward movement. Forward movement to the forward position causes the pin 136a to once again ride on the shaft of the probe 500a. If a second detent 520 is provided for the most forward position of the probe, the pin 136a will engage in that detent. When the probe 500a is moved backward towards its retracted position, the pin 136a rides along the shaft surface and again engages detent 518. However, this time, because of the hereinafter described arrangements of the detent 518 and the locking pin 136a, additional backward movement is more difficult; i.e., the lock is a better lock and requires more force. In this manner, the practitioner is made aware that the probe 500a is in the retracted position, and a stable retracted position is established.

Figure 5D:
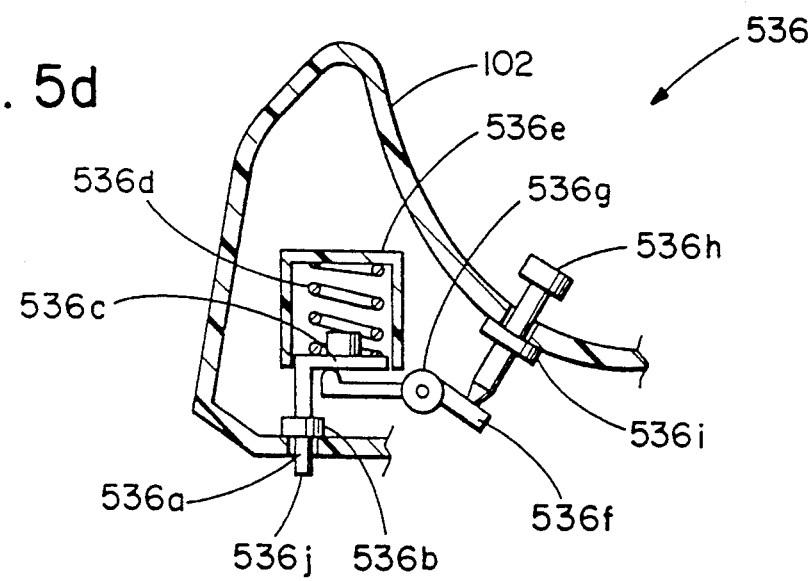
FIG. 5d is a cross-sectional view of a locking mechanism for an alternative embodiment for holding a probe in first and second positions in the fluid chamber.

FIG. 5d shows an alternate embodiment of the locking pin mechanism. In the embodiment of FIG. 5d, pulling on the probe will not release the probe from the locking pin. Rather, the locking pin mechanism 536 requires an active release. In particular, the locking pin mechanism of FIG. 5d, includes a locking pin 536a with a flange 536b and tab 536c, a spring 536d, a stationary spring stop or housing 536e, a lever 536f, a lever pivot 536g, and a button plunger 536h having flange 536i. With the provided arrangement, the locking pin 536a is spring biased by the spring 536d (which sits between housing 536e and tab 536c) so that the end of the locking pin 536a extends through housing 102 and can engage a detent in a probe. The flange 536b on the locking pin 536a stops the locking pin in a defined position. When the locking pin 536a is locked in a detent or groove of a probe, pushing on the plunger 536h (which also extends out of housing 102) releases the probe. The probe is released, because by pushing on lever 536f, the lever 536f rotates around pivot 536g, and pushes the locking pin 536a upwards by its tab 536c against the force of the spring 536d. Upon release of plunger 536h, the spring 536d forces the locking pin 536a downward until the pin is stopped by flange 536b. Likewise, lever 536f is pushed in the opposite direction, and pushes button plunger 536h upward until it is stopped by flange 536i.

Because the locking pin 536a is preferably angled at its tip 536j, and the detent (as seen in FIG. 9a) of the probe is preferably similarly ramped as it extends in a proximal direction, as the probe is pushed into the instrument, the locking pin 536a rides on the shaft, and into and out of the detent. Upon trying to remove the probe from the instrument, the blunt face of tip 536j will engage a shoulder on the detent, and removal by pulling on the probe will not be effective. Removal is only obtained by activation of plunger 536h.

Figure 6D:
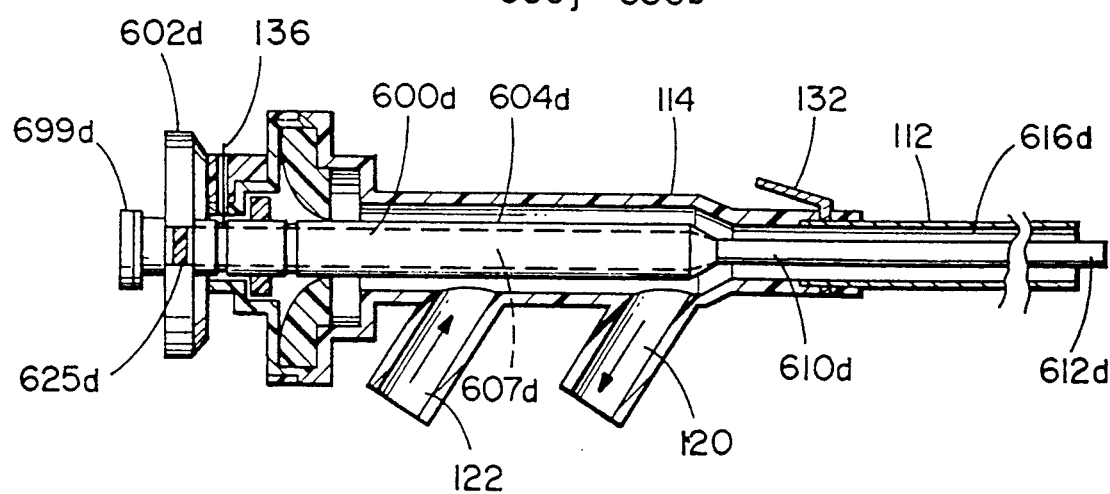

FIGS. 6a through 6d show some of the different types of probes which can be used with the instrument of the invention. In particular, and with reference to FIG. 6a, a probe 600a which is similar to probe 500a (FIGS. 5a and 5b) is shown, but two sets of lateral holes 606a, 607a, two O-rings 608a, 609a, and an inner tube 605a with a distal port 613a are provided. With the two O-rings, three chambers are established, with a distal chamber forward the O-ring 609a, a suction chamber between O-rings 609a and 608a, and an irrigation chamber proximal O-ring 608a. As shown in FIG. 6a, holes 607a in the probe communicate with the interior of hollow rod or tube portion 610a of the probe which extends through chamber 112. Thus, suction is accomplished through tube 610a, holes 607a and into suction port 120. Holes 606a, on the other hand, communicate with the annular space 616a in the cannula 112 via tube 605a which extends through the suction chamber and opens at 613a into the annular space 616a. Thus, in this probe 600a as compared to the probe 500a of FIGS. 5a and 5b, suction is applied through the smaller diameter portion of probe 610a and irrigation is supplied through the annular space 616a; which arrangement is the opposite of what is obtained in FIG. 5a.

FIG. 6b shows yet another kind of probe 600b. In this probe, suction and irrigation are both applied through the distal opening 612b of the probe 600b. Probe 600b is provided with lateral holes 606b communicating with the interior of the probe to the opening 612b at its distal end. O-ring 708b seals the fluid chamber 114 from the annular space 616b between probe 600b and cannula 112. Both suction and irrigation are provided through holes 606b to the opening 612b at the distal end of probe 600b.

FIG. 6c shows an additional feature which can be utilized in conjunction with any of the previously described probes. In particular, a probe 600c is shown (similar to probe 500a of FIG. 5a) with a longitudinal bore 607c which extends all the way through the shaft 604c and handle 602c. Blocking the longitudinal bore 607c in the handle (although it could be placed in the shaft) is a slit valve 625c. As shown in FIG. 6c, another probe, such as needle probe 689c, is inserted through the handle 602c, the slit valve 625c, the longitudinal bore 607c and into the hollow rod 610c. Probe 689c is typically longer than probe 600c so that when inserted in probe 600c, its distal end 691c extends through and beyond the opening 612c at the distal end of probe 600c. The proximal end of probe 689c is preferably provided with a female luer slip or luer lock 699c for receiving a syringe. With the provided arrangement, should an injection of medicine through the instrument 100 be desired, or should a fluid sample be required, a syringe can be coupled to the luer lock 699c, and the medicine injected or fluid aspirated into the syringe. After the injection or aspiration procedure, the needle probe 689c can be removed, and the probe 600c can remain in place without leakage out the proximal end because of the slit valve 625c. Likewise, before the needle probe 689c is inserted through the slit valve, and while the needle probe is extending through the slit valve, no leakage will occur even if suction or irrigation is occurring at the same time. It will be appreciated, that if desired, a gasket (not shown) can also be used in conjunction with the slit valve 625c in the handle of the tool 600c such that the arrangement will be similar to the proximal end of the fluid chamber. Also, it will be appreciated that the probe 600c can take many forms, with or without lateral ports (shown in phantom) and with or without O-rings as discussed above with reference to FIGS. 5a-5c. The O-rings could serve both to center the probe 600c and to separate the irrigation and suction ports.

FIG. 6d shows yet another kind of probe 600d which has some functional similarity to the probe 600c of FIG. 6c. In probe 600d, a fluid path 607d is provided through the handle 602d and shaft 604d and out through the hollow rod 610d to the distal opening 612d, and a slit valve 625d and a luer lock 699d are provided at the distal end of the probe 600d. If desired, medication can be injected through the probe 600d, or fluids can be sucked through the probe by coupling a syringe (not shown) to the luer connector connector 699d, with the nose of the syringe (not shown) extending through the slit valve 625d. By requiring the nose of the syringe to extend through the slit valve 625d, the syringe will be in fluid contact with the fluid path 607d in the shaft 604d. It will be appreciated that if the probe 600d is made sufficiently narrow, both suction and irrigation can be accomplished via the annulus established between the probe and the fluid chamber (and probe and cannula). If it is desired to have the probe 600d only permit suction besides its medicating and aspirating functions, an O-ring can be provided between the suction and irrigation ports.

It will be appreciated by those skilled in the art that yet other probes can be provided with the provided instrument. For example, a sharp trocar (e.g., a pyramidal metal trocar—not shown) can be formed as a probe and can be inserted and locked into place (as discussed above with reference to FIG. 5c or otherwise) in instrument 100 so that the sleeve 110 can act as the trocar tube. The instrument 100 with such a trocar probe in place can then act as a trocar which is used to make a trocar incision through the skin and fascia of a patient, and into a body cavity. Once the incision is made, the trocar probe can be released and removed, and the suction/irrigation instrument 100 can be used as aforedescribed, with probes and/or laparoscopic and endoscopic instruments (discussed below with reference to FIGS. 10a-10c) being inserted therethrough, except that instead of operating through a trocar tube, the sleeve 110 acts as the trocar tube. With such an arrangement, it may be desirable to eliminate the holes in the distal end of the sleeve 110. Likewise, it may be desirable to fix the sleeve 110 relative to the metal cannula such that the sleeve 110 cannot be retracted and rub against the incision. Other arrangements, such as providing the instrument with an extra tube (not shown) outside the sleeve 110 which acts as the trocar tube, etc. will suggest themselves to those skilled in the art.

Figure 7A:
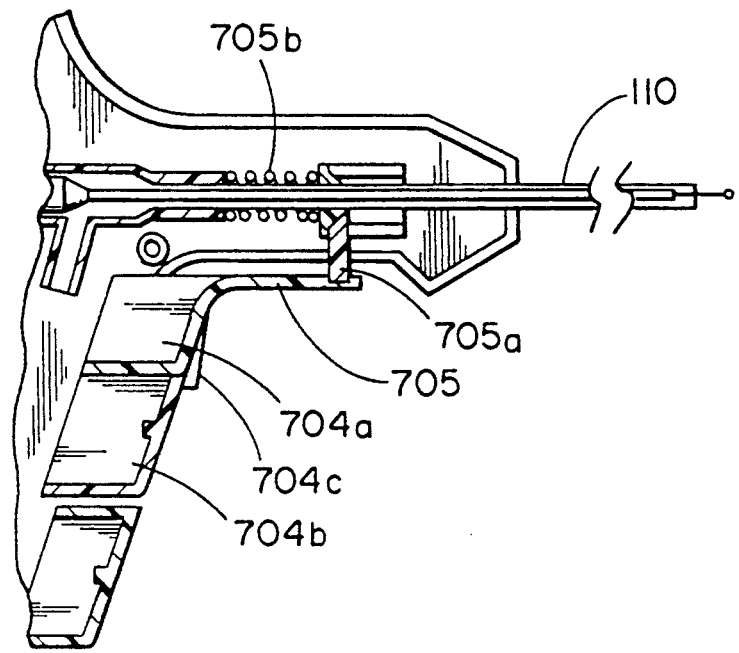
FIGS. 7a and 7b show alternate embodiments of suction triggers and mechanisms for activating a "supersuction" mode.
Figure 7B:
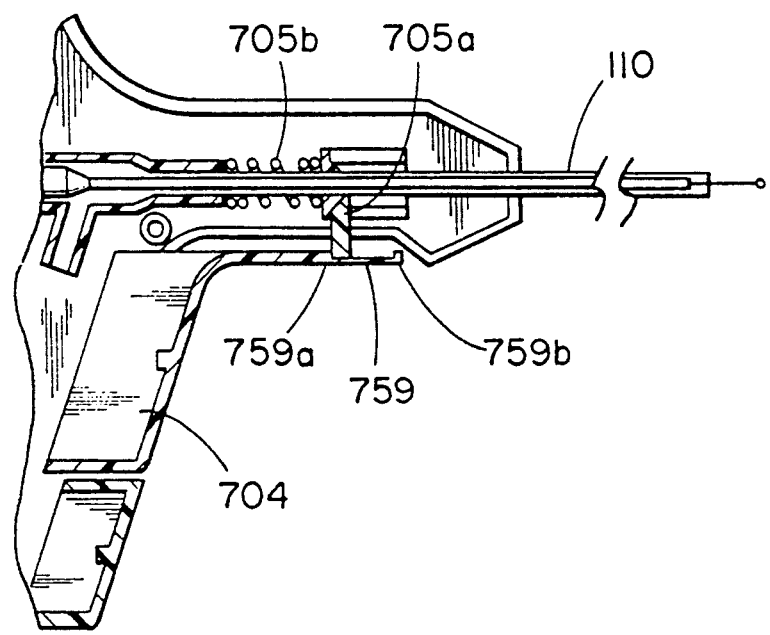

As mentioned above in reference to FIG. 1b, trigger switch 104 may be divided into two portions 104a and 104/104d which control suction and "super suction". Three different embodiments for providing the "super suction" feature are seen in FIG. 1b, FIG. 7a and FIG. 7b, and all may be understood with further reference to FIGS. 2a, 2b, and 2c.

Figure 2A:
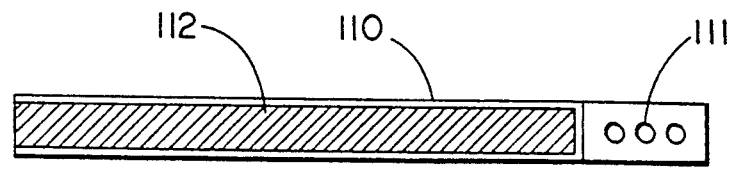
FIGS. 2a, 2b, and 2c are respectively a partially cutaway side view and side views which show the distal end of the cannula and the sliding sleeve of the instrument of FIG. 1 in first, second and third relative positions which respectively represent a regular suction mode, and first and second "supersuction" modes respectively.
Figure 2B:
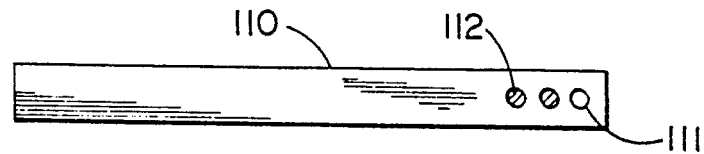
Figure 2C:
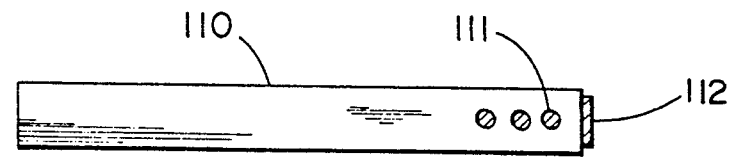

FIGS. 2a and 2b show the distal ends of cannula 112 and sliding sleeve 110 in cross section. FIG. 2a shows the default position of cannula 112 and sliding sleeve 110 when no trigger switches are being pulled. In FIG. 2a, it is seen that suction may occur through all of the holes 111 in the sliding sleeve. Material sucked therethrough then proceeds through the distal opening in the cannula, as there is no annulus between the cannula and the sliding sleeve (i.e., they are in sliding contact with one another). FIG. 2b shows an intermediate position, where sliding sleeve 110 is retracted such that at least one hole 111 in the sliding sleeve 110 is blocked by the cannula 112, but suction can be obtained through other holes therein. FIG. 2c shows a full "super suction" position, where the sliding sleeve 110 is completely retracted such that all of the holes 111 in the sliding sleeve 110 are blocked by the cannula 112, and suction is only through the distal opening in the cannula 112.

As previously mentioned, the distal end of sliding sleeve 110 is provided with a plurality of lateral holes 111. When sleeve 110 is in the position shown in FIG. 2a, the suction vacuum appearing at the distal tip of cannula 112 is diffused. When sleeve 110 is pulled back to the position shown in FIG. 2c, the lateral holes 111 of sleeve 110 are blocked and can no longer provide suction openings. Thus, the entire suction vacuum appears at the distal tip of cannula 112 to effect "super suction". It will be appreciated that as sleeve 110 slides over cannula 112, holes 111 will at different positions (e.g., FIG. 2b) have incremental effects on the suction at the distal tip of cannula 112. Thus, the operation of the "super suction" feature of the invention is incremental and as the super suction trigger is pulled, suction gradually increases until a maximum is reached.

The preferred embodiment for generating the super suction function is shown in FIG. 1b. In this embodiment, the sliding sleeve 110 is provided with a collar 105a which is directly coupled to a super suction trigger 104a. The collar 105a is spring loaded by spring 105b so that in the default position, the sleeve 110 assumes the position as shown in FIG. 2a, and the trigger 104a is located distally relative to an extension 104d on the suction trigger 104. With this arrangement, sliding sleeve 110 can be moved a certain amount by pulling trigger 104a without engaging suction trigger 104. This may be desirable in order to clean debris which may accumulate at the distal end of sliding sleeve 110. Continued movement of trigger 104a backward, however, will eventually cause the super suction trigger 104a to engage the extension 104d of trigger 104, thereby automatically activating suction. On the other hand, the suction trigger 104 can be activated without activation of the super suction trigger 104a.

A second super suction embodiment is seen with reference to FIG. 7a. In FIG. 7a, the super suction trigger switch 704a is coupled to a hook 705 which engages collar 705a of sliding sleeve 110. As with the embodiment of FIG. 1b, the collar 705a is spring biased by a spring 705b. The super suction trigger switch 704a is also provided with an extending portion 704c which extends over the suction trigger 704b. In this manner, the action of pulling trigger switch 704a, which pulls back collar 705a against spring 705b, always causes sliding sleeve 110 to slide backward (as seen in FIGS. 2b and 2c) while at the same time causing trigger switch 704b to open suction valve 124. As with the arrangement of FIG. 1b, the pulling of trigger switch 704b will not cause the super suction trigger 704a to be activated.

A third embodiment of super suction can be effected without dividing the trigger switch into two portions as shown in FIGS. 1b and 7a. In FIG. 7b, the trigger switch 704 is attached to an actuator mechanism 759 having two extensions 759a and 759b which are spaced apart and surround collar 705a with a gap being formed between collar 705a and extension or hook 759b. The collar 705a is attached to the proximal end of the sleeve 110 and is spring loaded by spring 705b. In the embodiment of FIG. 7b, when trigger 704 is pulled through a distance equal to the gap between hook 759b and collar 705a, the suction valve is opened, but the sliding sleeve 110 is not pulled. Additional squeezing of trigger 104 beyond that point, however, causes hook 759b to engage collar 105a and slide sleeve 110 back against spring 105b causing super suction. Thus, with the embodiment of FIG. 7b, full suction can be obtained by squeezing trigger 704 a first amount (fully opening the valve), while super suction is obtained by squeezing trigger 704 even further to cause movement of sleeve 110 after the valve is fully opened.

Figure 8A:
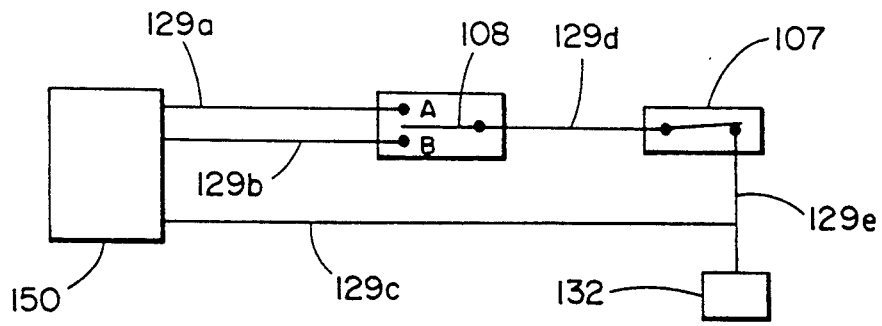
FIG. 8a is a schematic diagram of the electrical circuit incorporated in and coupled to the instrument of the invention, including a irrigation/cautery override mechanism.

FIG. 8a shows a block diagram of the electrical circuit used with the instrument to power an electrosurgical probe. An electrical source 150 supplies two different DC voltages through conductors 129a and 129b to a three position (A-OFF-B) switch 108 which selects either voltage A or voltage B. Switch 108 supplies the selected DC voltage through conductor 129d to safety switch 107 which is normally closed and thereby supplies the voltage through conductor 129e to electrical contact 132 and back to electrical source 150 via conductor 129c. Electrical source 150 then senses which DC voltage was selected and supplies the appropriate AC voltage for cutting or coagulating via conduit 129c back to electrical contact 132 whereby an electrosurgical probe receives the selected voltage. As seen in FIG. 1b, the safety switch 107 is opened whenever irrigation trigger 106 is pulled, as spring 107a, which is fixed to the irrigation trigger 106 at point 107b, and anchored to the housing at 107c, is provided with an actuation portion 107d which moves off of dome switch 107 when spring point 107b is moved. Thus, cautery is interrupted during irrigation. In this regard, it is recommended that the valves discussed above with reference to FIGS. 3a and 3b and also discussed below with reference to FIG. 13 be provided with a certain amount of travel before irrigation is actuated. This will ensure that the safety switch is opened before any irrigation fluid is allowed to flow through the irrigation valve. Moreover, it should be noted that this arrangement of the electrical source 150 and conductors 129a-e ensures that the actual AC cautery voltage does not pass through the switches 107, 108, thereby minimizing the risk of shock to the physician and switch failure. Such electrical sources which are activated by DC voltage to send a selected AC voltage are known in the art.

Figure 8B:
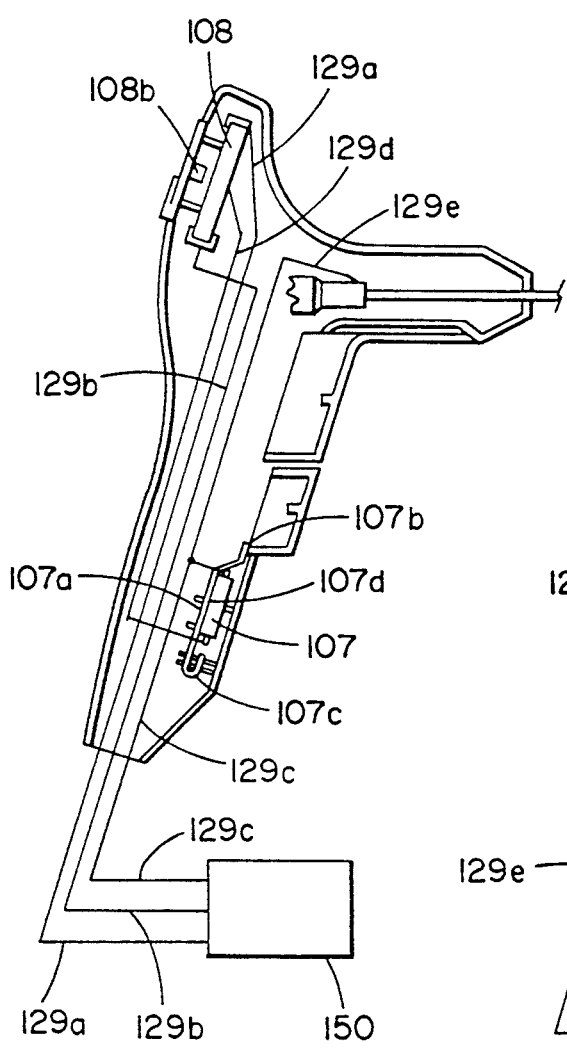
FIGS. 8b and 8c are schematic diagrams showing how a portion of the circuit of FIG. 8a is embodied in the shell of the instrument of the invention.
Figure 8C:
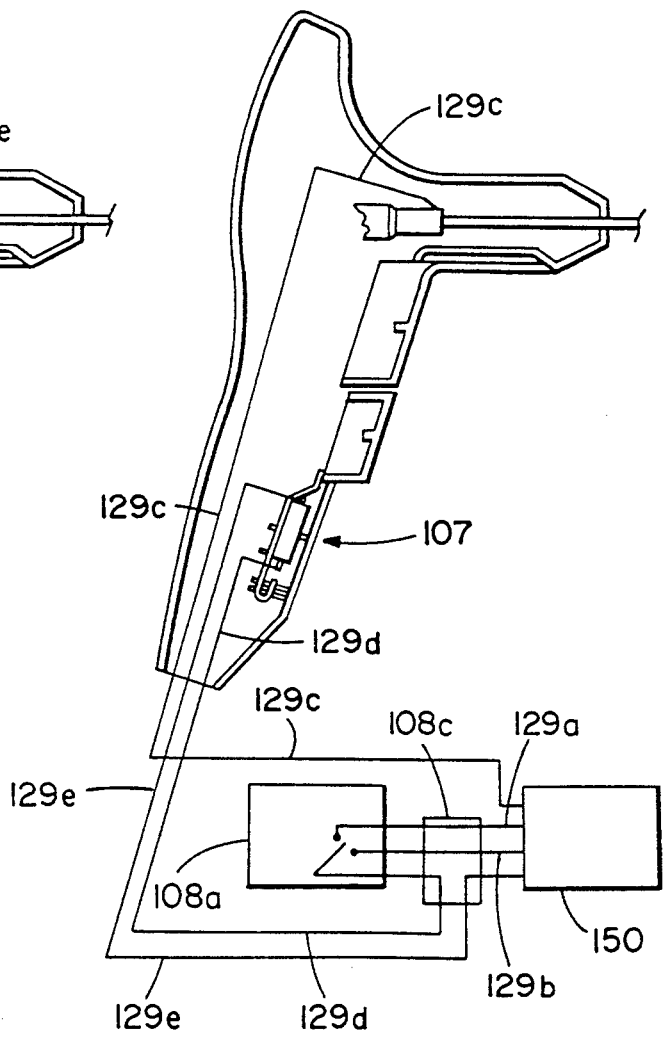

FIGS. 8b and 8c show examples of how this circuit is implemented in the shell of the instrument. Turning to FIG. 8a, an electrosurgical power supply 150 provides two sources of DC voltage through conductors 129a and 129b. These voltages are selectively applied to the electrical source 150 via conductor 129c by a three position switch 108 which in FIG. 8b is a rocker switch 108b. Switch 108 selects the desired voltage and conducts that voltage through conductor 129d to safety switch 107 which is normally closed but is opened by pulling the irrigation trigger 106. Safety switch 107, when closed, couples conductor 129d, electrical contact 132 through conductor 129e, and electrical source conductor 129c. Electrical source 150 then senses which DC voltage was selected by switch 108 and supplies the appropriate AC cautery voltage through conductor 129a, switch 107 and conductor 129e to electrical contact 132 and thereby to an electrosurgical probe inserted in the shell 102.

FIG. 8c shows a similar arrangement to FIG. 8a, but with a standard foot switch 108a and a provided adapter 108c substituted for the thumb switch 108 of FIG. 8a and 8b. As seen in FIG. 8c, the standard electrosurgical power supply 150 is provided with four output ports: a first port for a "cut" low voltage wire 129a; a second port for a "coag" low voltage wire 129b; a third port for a "common" wire 129e; and a fourth port for the high voltage AC signal wire 129c. Likewise, the standard foot switch 108a is provided with three ports, including the "cut" port, the "coag" port, and the "common" port. The primary difference between the electrical arrangement of FIG. 8c and that of FIGS. 8a and 8b is that in FIG. 8c, the low voltage DC cut or coag signal is not sent over the same wire as the AC signal. Thus, wire 129c is connected directly from the power supply 150 to the cannula, and the adapter 108c is provided to interrupt the common wire 129d/129e, so that it is routed through the cautery override safety switch 107. When switch 107 is closed, and either the cut or coag foot switch is pressed, a DC circuit is completed from power supply 150, through wire 129a or 129b (via adapter 108c), through wire 129d (via adapter 108c), through switch 107, through wire 129e (via adapter 108c) and back to the power supply 150. The closed circuit signals the power supply 150 to provide an appropriate AC signal to the cannula of the instrument via wire 129c. However, when switch 107 is open, the DC circuit cannot be completed, and hence no high voltage AC signal will be sent out over wire 129c.

While not preferred, it will be appreciated that in either of the disclosed arrangements, switch 107 can be located in the AC path 129c instead of the DC path. Such an arrangement guarantees that the voltage/current source 150 cannot malfunction and supply current via the AC path 129c to the cannula when no DC voltage is being presented. On the other hand, such an arrangement places greater electrical demand on switch 107 as switch 107 must interrupt the high voltage AC current.

Figure 8D:
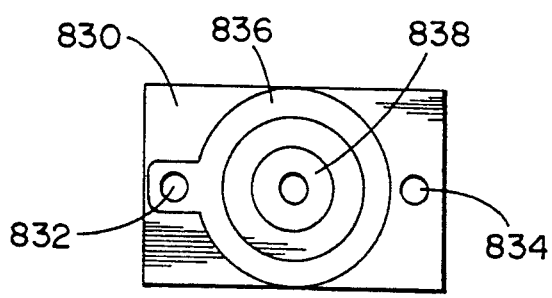
Figure 8F:
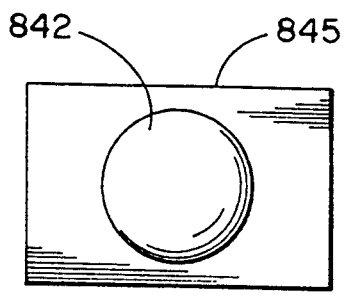
Figure 8E:
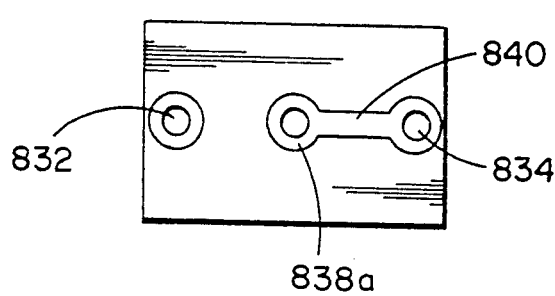
Figure 8G:
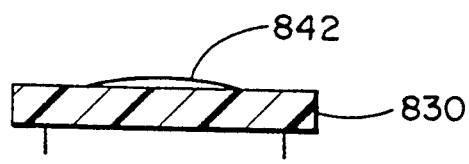

FIGS. 8d–8k show preferred embodiments dome type switches which can be used for the thumb switch 108 and safety switch 107 described above. In particular, FIGS. 8d and 8e represent respectively a top view and a bottom view of a printed circuit board 830 used in connection with dome-type safety switch 845 shown in FIGS. 8f and 8g. This switch may be used for safety switch 107 (FIG. 1b). Circuit board 830 includes wire holes 832, 834 for attaching electrical wires. Wire hole 832 is surrounded by conductive material 836 forming a circular strip surrounding but insulated from a smaller conductive circle 838. In FIG. 8e it can be seen that the small conductive circle 838 is coupled by conductive material 838a through conductive strip 840 to wire hole 834.

FIG. 8f shows a top view of dome switch 845 having a dome 842. As will be appreciated, dome 842 is constructed of resilient material and is conductive on its side facing the top of circuit board 830 so that pressing dome 842 electrically couples the conductive material 836 and 838 thereby coupling wires attached to wire holes 832 and 834. Referring once again to FIG. 1b, it can be seen that a dome type switch such as the one described above my be used for safety switch 107 wherein a biasing member 107a such as a spring keeps switch 107 normally closed and where the biasing member has an engaging portion 107b which is moved by trigger 106 so as to move actuation portion 107d and open the switch 107.

Figure 8H:
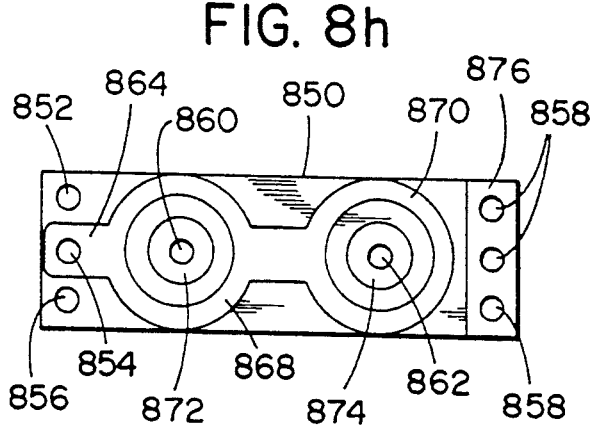
Figure 8J:
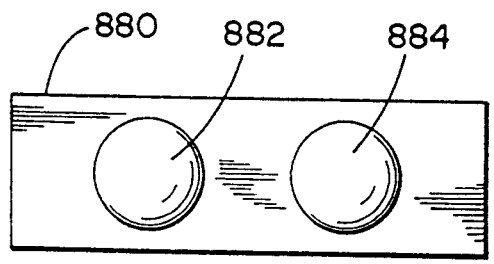
Figure 8I:
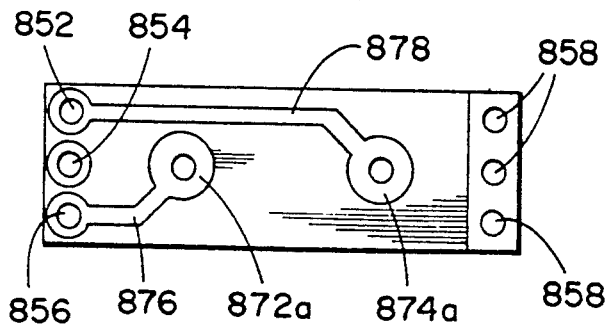
Figure 8K:
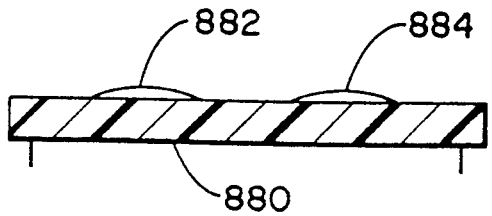

FIGS. 8h and 8i are respectively a top view and a bottom view of a printed circuit board 850 used in connection with dometype rocker switch 880 shown in FIGS. 8j and 8k. Circuit board 850 includes wire holes 852, 854, and 856 for connecting to electrical wires. Wire hole 854 is surrounded by conductive material 864 which is a straight strip connecting two circular strips of conductive material 868 and 870. These circular strips surround smaller conductive circles 872, 874. A single conductive strip 876 surrounds wire holes 858. In FIG. 8i it is seen that wire hole 852 is surrounded by conductive material 878 which connects with conductive material 874a and 874 on the top side of the circuit board. Similarly, wire hole 856 is surrounded by conductive material 876 which connects with conductive material 872a and 872 on the top side of the circuit board.

FIG. 8j shows a top view of the dome switch 880 having domes 882 and 884. As will be appreciated, domes 882 and 882 are constructed of resilient material and are conductive on their side facing the top of circuit board 850 so that pressing dome 882, for example, electrically connects conductive material 868 and 872 thereby coupling the cautery wires connected to wire holes 854 and 856. Similarly, pressing dome 884 results in a coupling of conductors connected to wire holes 854 and 852. Wire holes 858 are provided as a simple hardwire connected means to couple three conductors. Referring once again to FIG. 1b, it can be seen how a two-dome-type switch such as the one described above can be used for thumb switch 108 wherein a rocker arm 108a pivots at 108b to depress either one of the domes described above.

As mentioned above, many different kinds of probes can be used with the instrument and more than one probe can be used together in the instrument. FIGS. 9a–9g show additional features of probes used with the instrument.

FIG. 9a shows a side cross sectional view of a cautery probe 900. The probe comprises a handle 902, from which extends a shank 904 which carries the probe wire or conductor 906. Handle 902 is provided with a recess 902a for receiving a color coded insert 903 which snaps in place. In this manner, the distal arrangement of the probe can be quickly identified by the physician during an operation either while the probe is in place, or in choosing a probe. The shank 904 is provided with at least one locking groove 918 to secure the probe in the instrument as discussed above in reference to FIGS. 5 and 6, although a second groove 920 may also be utilized. The probe conductor 906 is provided with a bumped portion 911 for engaging the electrified cannula 112 as discussed above, and terminates with a cauterizing surface 912 which may be configured in a number of ways. The probe conductor 906 is insulated with insulating sleeve 908 along its entire length except for the bumped portion 911 and the cauterizing surface 912. Preferably, the bumped portion 911 is located near the distal end of the probe to add stabilization to the probe. However, if desired, in accord with another embodiment of the invention, the instrument 100 is not provided with a metal cannula and a sleeve, but with only a smooth nonconductive sleeve which acts as the cannula. With this arrangement, the bumped portion 911 of probe 900 is provided close to the shank of the probe at the location of the washer 132 (FIG. 4) so that the bumped portion 911 contacts the washer 132 to obtain its electrification.

Referring now to FIG. 9b, the shank portion 904 of the probe 900 is seen in an enlarged view. As shown in FIG. 9b, and previously discussed with reference to FIGS. 5a–5c, the locking groove or detent 918 in probe shank 904 is configured such that it engages and easily disengages the locking pin 136 when the probe is inserted, but does not as easily disengage when the probe is being withdrawn from the fluid chamber. In particular, locking groove 918 has a first ramp 918a of decreasing diameter as it extends distally, followed by a section of constant diameter 918b followed by a sharply angled ramp or step 918c of increasing diameter. By forward movement of the probe carrier 904, the locking pin rides on the outer surface of the probe. Upon reaching groove 918, the locking pin snaps into the groove. Continued movement causes the pin to ride up the gentle slope of the proximal ramp 918a and to continue riding on the outer surface of the probe shank 904. Upon rearward movement of the probe, however, the pin located in the groove 920 and establishes a stable intermediate position for the probe. If it is desired to remove the probe, the pin must be forced over the step or sharply angled ramp 918c. It will be appreciated by those skilled in the art that locking groove(s) 918 (and 920) and/or locking pin 136 may be configured in different ways to give probes a different feel when engaging locking pin 136.

As mentioned above, the cauterizing surface 912 of the probe 900 may be configured in a number of ways. Surface 912 in FIG. 9a is a ball shaped tip. FIGS. 9c–9f show respectively a hook 912a, an L-hook 912b, a spatula 912c and a spoon 912d. Other configurations will be obvious to those skilled in the art. The color coded inserts 903 mentioned above are preferably used as a rapid means of distinguishing these probes when the probe is inserted in the instrument and not in view, or when many of the probes are laying together on a tray.

FIG. 9g shows another kind of probe 901. This probe has a retractable probe conductor 906 which is slidably mounted inside a hollow opening 925 of probe shank 924. Probe conductor 906 is provided with a proximal handle 930 which is biased by spring 926 to a position wherein probe conductor 906 is somewhat retracted inside probe shank 924. Probe handle 902 is provided with a hollow opening 927 which receives the proximal handle 930 and a movable pin 928 biased radially outwards by spring 929. Proximal handle 930 is provided with lateral openings 932 through which pin 928 passes in part but is stopped by pin stop 931 and lateral opening 932 is provided at its proximal end with a pin stop engaging recess 933. As shown in FIG. 9g, the probe conductor 906 is retracted, and proximal handle 930 is biased outward from probe handle 902 and pin 928 is biased radially out of probe handle 902 until pin stop 931 rides against the edges of lateral opening 932. By pressing proximal handle 930 forward into probe handle 902, probe conductor 906 is moved in the distal direction out from its retracted position shown. As a result, spring 926 is compressed, and inner surface of lateral opening 932 rides on top of pin stop 931 until pin stop 931 is positioned above pin stop engaging recess 933. At this point, pin 928 moves radially outward under the action of spring 929 and pin stop 931 engages pin stop engaging recess 933 whereby the position of proximal handle 930 is locked against spring 926 and the probe conductor 906 is locked in an extended position. It will be appreciated that the retraction of the probe conductor 906 may be simply effected by pressing pin 928 at its top portion which extends radially through probe handle 902, thereby disengaging pin stop 931 from pin stop engaging recess 933 and allowing action of spring 926 to bias proximal handle 930 back to the position shown in FIG. 9g. It will be appreciated, that in order to avoid entry of fluid into the probe 901, a fluid seal 935 such as an O-ring is provided in the shank 924. The seal contacts the probe conductor 906, but permits the probe conductor 906 to extend therethrough.

As mentioned above, in addition to the probes specifically designed for use with the instrument, many existing endoscopic tools can be used in conjunction with the instrument and other tools may be modified for use with the instrument. For example, FIGS. 10a–10c show details of endoscopic tools from coassigned U.S. patent applications Ser. Nos. 07/780,013 and 07/837,046, both of which are incorporated herein by reference in their entireties.

With reference to FIG. 10a, a laparoscopic surgical tool is indicated at 1000. The laparoscopic surgical tool 1000 includes an aluminum tube 1015 surrounded by a peripheral insulating shrink wrap layer of plastic 1020, a clevis means 1030, end effectors 1040, actuating means 1050, and a push rod 1060. The clevis means 1030 is preferably a separately formed aluminum piece which fixedly engages aluminum tube 1015. The clevis 1030 also engages the manipulating members 1090, 1092 of the end effector 1040. Members 1090 and 1092 are pivotally engaged to clevis 1030 at pivot pin 1045. The push rod 1060 is engaged at its distal end 1065 to the manipulating members 1090, 1092, and is connected at 1070, at its proximal end, to a manually operable actuating means 1050. As seen in FIG. 10a, (as opposed to Ser. No. 07/780,013) instrument 1000 is modified in that a bump 1011 in the aluminum tube 1015 is provided to make contact with cannula 112 shown and described above, and in that the insulation 1020 is discontinued at the bump.

In use, the laparoscopy tool 1000 is inserted with the blades 1090, 1092 of the end effector 1040, in the closed position, through the elastomeric gasket and slit valve and into the fluid chamber and cannula of instrument 100 (shown and described above). Upon the distal portion of the laparoscopy tool 1000 exiting the cannula of instrument 100, one or both of the blades 1090, 1092 can be opened and closed as indicated by reciprocal motion of push rod 1060 which results from operation of the manual actuating means 1050, and the laparoscopy tool 1000 may be rotated as desired. If the laparoscopy tool is sufficiently small in diameter relative to the cannula, suction and irrigation are still available through the cannula 112. In addition, because of bump 1011, a cautery voltage may be selectively applied to the end effector of the laparoscopy tool 1000 through electrical contact 132 and cannula 112. Further, the laparoscopy tool 1000 may be partially withdrawn from, but left in instrument 100 with the elastomeric gasket and slit valve sealing the fluid chamber and preventing leakage, and the laparoscopy tool 1000 may be reinserted or fully withdrawn as desired. Then, other tools may be inserted through instrument 100.

With reference to FIGS. 10b and 10c, a biopsy forceps assembly 1100 is seen which is a modified version of the biopsy forceps device shown in previously incorporated patent application Ser. No. 07/837,046. Biopsy forceps tool 1100 has a distal end 1112 having a jaw assembly 1114, and a proximal end 1116 having a handle 1117, a spool 1119, and a thumb ring 1121 for manipulation of the jaw assembly. The jaw assembly 1114 comprises a pair of jaws 1118 and a clevis 1134. The jaws 1118 are preferably investment cast, and are preferably a duplicate of the other. Each jaw 1118 has a proximal end having a tang 1124 through which a bore 1166 transversely extends. In addition, jaws 1118 each include a second transverse bore 1130 through a middle portion of the jaw. A clevis pin 1128 extends through bore 1130 and couples to the arms of the clevis 1134. As seen in FIG. 10c, the clevis 1134 extends proximally into a hub 1140 which also receives metal tube 1150. Metal tube 1150, as shown in FIG. 10b, is provided with a bump 1151 for cautery pickup from the cannula 112 (FIG. 1).

In order for the jaws 1118 to rotate around clevis pin 1128, they must be actuated at their tangs 1124. In particular, a pair of pull wires 1160 are provided at their distal ends with dog's-leg bend (a Z-bend). Thus, each pull wire 1160 has a first portion 1162 which is rotatably disposed in the recess 1126 in the tang 1124 of each cutter jaw 1118, a second portion 1164 which extends through the bore 1166 in the most proximal end of the tang 1124, and a ninety degree bend 1168 between the second portion 1164 and the main pull wire 1160. Each pull wire 1160 is also preferably provided with a reflex curve 1170 extending between their distalmost ends and the distalmost end of the tube 1150. The reflex curve 1170 helps to open the cutter jaws 1118 when the spool 1119 on the handle 1117 is displaced distally thereto.

The proximal end of the tube 1150 and the proximal end of the pull wires 1160 extend into handle 1117 which is located at the proximal end 1116 of the biopsy forceps assembly 1110. The handle 1117 comprises a central shaft 1121 about which a displaceable spool 1119 is disposed. Additional details of the handle may be obtained by reference to aforementioned Ser. No. 07/837,046 as they do not comprise an aspect of the present invention. It is of note, however, that movement of the spool 1119, which is disposed about the central shaft, effectuates movement of the puller wires 1160 disposed within the tube 1150. Because the distal ends of the puller wires 1160 are attached to the tangs 1124 on the jaws 1118, while the jaws are fixed relative to the metal tube 1150 by clevis 1134 and clevis pin 1128, movement of spool 1119 causes rotational movement of the jaws 1118.

In use, the jaws 1118 of the biopsy forceps tool 1100 are inserted in the closed position through the elastomeric gasket 119 and slit valve 118 and into and through the fluid chamber 114 and cannula 112 of instrument 100 (shown and described above). Upon the distal portion of the biopsy forceps tool 1100 exiting the cannula of instrument 100, jaws 1118 can be opened and closed as described above by movement of spool 1119. If the biopsy forceps tool 1100 is sufficiently small in diameter relative to the cannula, suction and irrigation are still available through the cannula 112. In addition, because of bump 1151, a cautery voltage may be selectively applied to the end effectors (jaws) of the endoscopic tool 1100 via electrical contact 132 and cannula 112.

It will be appreciated that the instrument of the present invention offers many advantages when used in endoscopic surgery. After providing an incision in the body and providing a trocar tube therein, the instrument 100 of the invention can be inserted into the trocar tube to supply irrigation and suction. Moreover, various endoscopic tools and probes can be inserted into the instrument through the fluid chamber 114 and cannula 112 as described above to perform endoscopic procedures while maintaining availability of irrigation and suction through the same body incision. As described, any of these probes or endoscopic tools can also be provided with electrosurgical voltages and currents through the instrument by contact with the electrical contact 132.

Figure 11A:
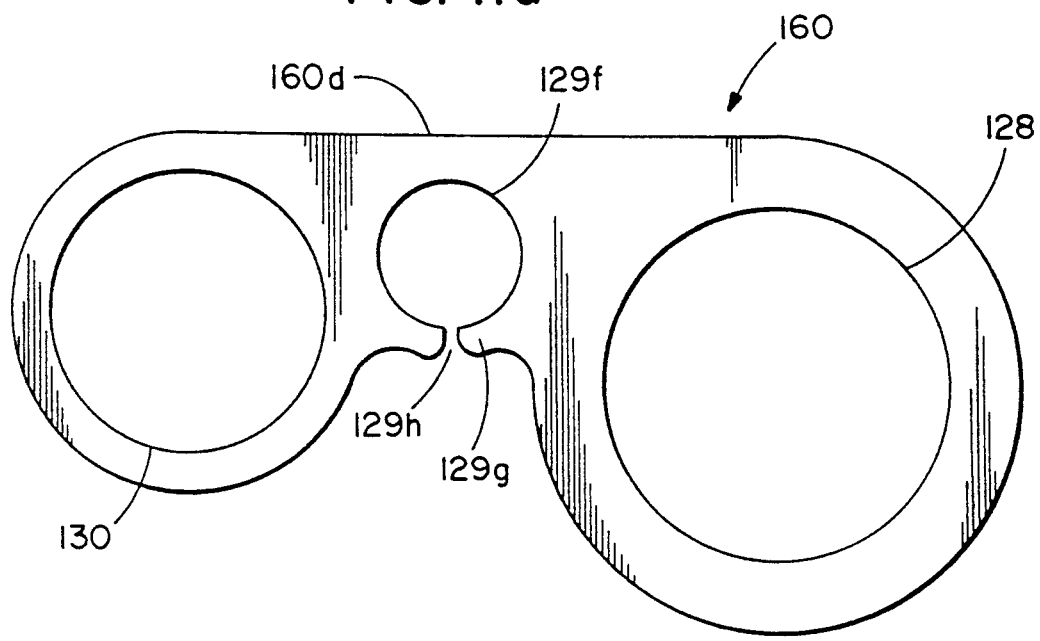
FIG. 11a is a cross-sectional view of a preferred molded tubing having suction and irrigation conduits which together surround a rib indenture into which a cautery wire is held.

As mentioned in reference to FIGS. 1a and 1b, and in accord with another aspect of the invention, an electrical supply 150, a vacuum 152, and an irrigation supply 154/156 can be connected to the instrument via a single "spinal cord" arrangement 160 where suction and irrigation are in two channels of a single molded plastic tube with a rib therebetween which carries the cautery wires. FIG. 11a shows a cross section of a preferred spinal cord tubing 160 having an irrigation supply tube 130 and a larger suction tube 128 molded together in a single piece with a cylindrical groove or space 129f for receiving electrical supply wires 129 (FIG. 1a). The groove 129f is mostly closed, but is provided with a slit opening 129h defined by a pair of lips 129g extending along the length of tubing 160 so that the electrical supply wires may be inserted into the space 129f. As seen in FIG. 11a, the size of the opening 129h between the lips is smaller than the diameter of cylindrical space 129f (and smaller than the diameter of the wire(s) 129). However, because the tubing and lips are elastic, the wire 129 may be forced past the lips and inserted and held in the space 129f, and remain secure therein although it is still removable therefrom.

Figure 11B:
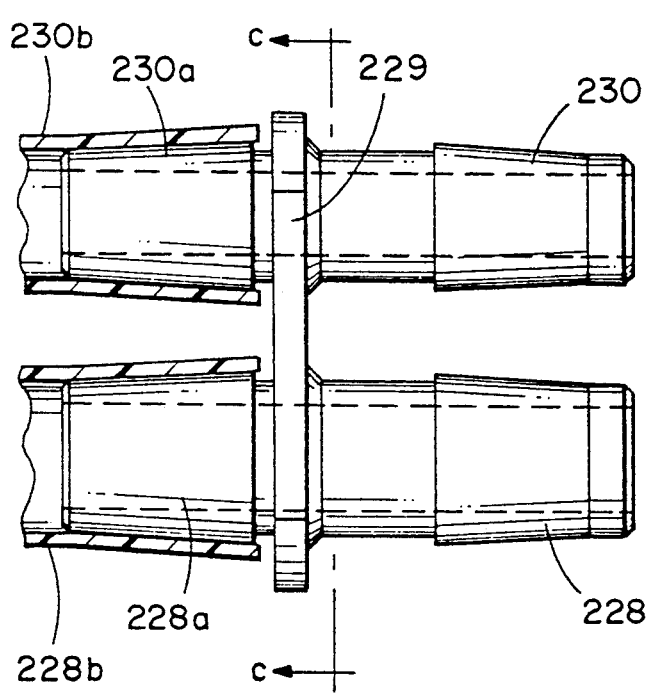
FIGS. 11b and 11c are side and cross-sectional views of a connector which mates with the molded tubing of FIG. 11a on the instrument side, and provides for separate suction and irrigation tubes and a loose cautery wire on a second side.
Figure 11C:
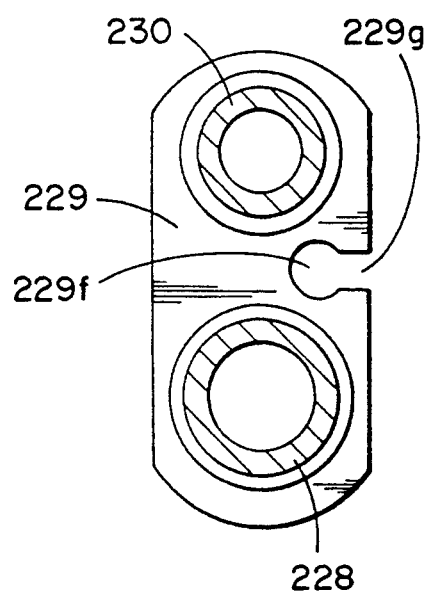

FIGS. 11b and 11c show a connector used for coupling the spinal cord tubing 160 to separate suction and irrigation tubes and for holding the electrical supply wires in place at their point of entry into cylindrical space 129f of the tubing 160. The connector comprises a central block 229 having tapered couplings 230 and 228 on one side for connection with irrigation and suction supply tubes 130 and 128, respectively, of the spinal cord tubing 160, and similarly tapered couplings 230a, 228a on the other side for connection with individual irrigation supply tube 230b and suction supply tube 228b. The diameter of the couplings may be varied depending on the connections to be made. For example, when the connector is used inside the instrument 100 (134 in FIG. 1b) the inwardly directed tapered couplings may be smaller to connect with tubes inside the instrument.

FIG. 11c shows the connector in cross section along line C—C of FIG. 11b. Here it can be seen that the aforementioned couplings have coaxial throughbores as would be expected and the central block 229 is provided with a wire space 229f having an opening 229g corresponding to the wire space 129f and opening 129g of the spinal cord tubing 160. This wire space 229f provides a convenient place to secure wires entering the space 129f of the tubing 160. The central block may also be provided with mounting holes, flanges and the like, for securing it in a particular place where the individual tubes and wires are joined to the spinal cord tubing.

Figure 11D:
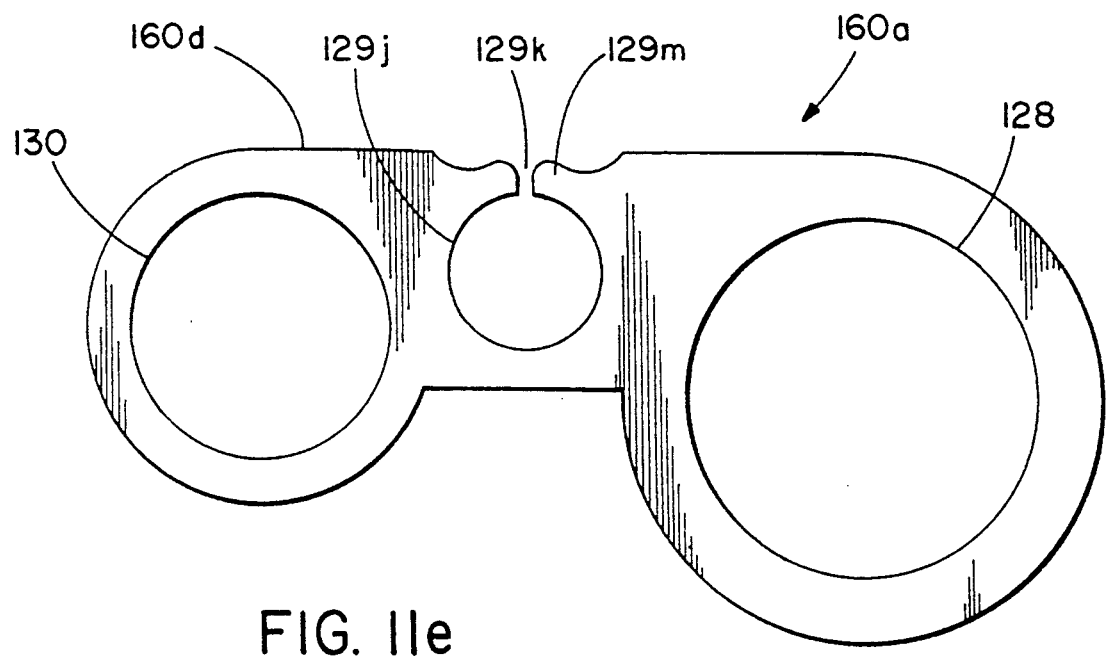
FIG. 11d is a cross-sectional view of an alternative molded tubing having suction and irrigation conduits which together surround a rib indenture into which a cautery wire is held.

FIG. 11d shows an alternate embodiment of tubing 160a with suction tube 128, irrigation tube 126 and a wire slot or space 129j. The difference between this embodiment and the one shown in FIG. 11a is that the opening 129k defined by lips 129m is on the opposite side of the tubing; i.e., the flat outer surface 160d of tubing 160 is interrupted by the lips 129m and slot opening 129k as opposed to presenting a flat outer surface as shown in FIG. 11a.

Figure 11E:
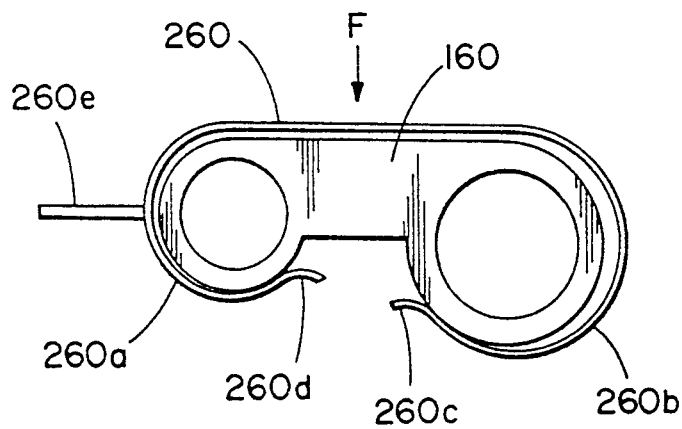
FIG. 11e is a cross-sectional view of a clip for the tubing of FIG. 11a with the tubing held therein.
Figure 11F:
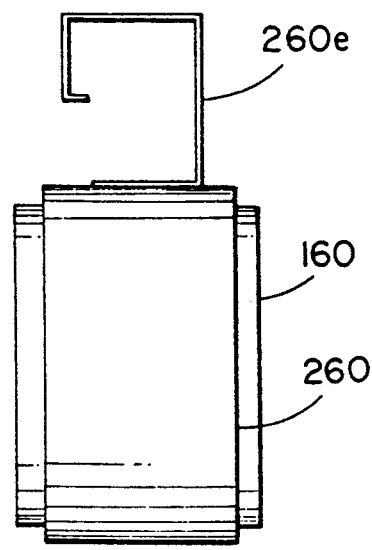
FIG. 11f is a view of the clip of FIG. 11e in the direction of arrow F thereof.

FIGS. 11e and 11f show a hanger clip 260 for securing the tubing 160 to the edge of an operating table or to a hanging post such as those used for IV bottles and the like. The hanger 260 comprises a resilient strip of metal or plastic shaped to conform somewhat to the round sides of the tubing by rounded portions 260a and 260b terminating in curved ends 260c and 260d. The tube is inserted into the clip by pulling the curved ends 260c and 260d apart and snapping the tube 160 through the space created between these ends. The resiliency of the clip and its conformity to the shape of the tube make it fit snugly around the tube. One end of the clip is provided with a hook like member 260e for hanging as stated above. Alternatively, the hook-like member 260e may be replaced with a spring-action grasping clamp or an adhesive strip or pad to allow the clip to be attached to the surgical drapes or to the operating table.

The hanger clip 260 or the like may also be used in conjunction with the tubing embodiments seen in FIGS. 11g and 11h. In FIG. 11g, a molded tubing 1560 is provided with a suction tube 1528, and an irrigation tube 1530. The tubes are joined at a thin junction 1570 which is defined by the meeting of the suction and irrigation tubes at points 1571a and 1571b. As seen in FIG. 11g, the thin junction 1570 is made sufficiently narrow such that the suction and irrigation tubes can be peeled apart. In addition, as seen in FIG. 11g, the irrigation tube has resilient extensions or lips 1540a, and 1540b which help define a lumen 1529 for a cautery cable having an opening 1540c which is smaller than the diameter of the cautery wire to be held in the lumen. In this manner, the wire (not shown) can be snapped into place and held in place, or removed as desired. It will be appreciated that the resilient lips are provided on the irrigation tube because the irrigation tube is preferably smaller than the suction tube, and so the overall diameter of the tube portion housing the irrigation tube and cautery lumen will be relatively close in size to the size of the suction tube portion. Of course, if desired, the lips defining the cautery lumen could be provided on the suction tube rather than on the irrigation tube.

Turning to FIG. 11h, a tubing 1660 which is similar to that of FIG. 11g is provided, except that instead of providing an integral single plastic tubing, two tubes 1628 and 1630 are provided. Suction tube 1628 is shown with lips 1671a and 1671b which define a thin channel. Irrigation tube 1630 is shown with a protrusion or knob 1670 which mates with the thin channel along its length. In this manner, the irrigation tube and suction tube 1628 are held together, but can easily be divided as shown. As with the embodiment of FIG. 11g, the suction tube 1630 is also provided with resilient lips 1640a and 1640b which define a lumen 1629 for a cautery cable, with the lumen having an opening 1640c which is smaller than the diameter of the cautery cable. In this manner, the cautery cable can be snapped into place, or divided out from the irrigation lumen as desired.

The tubings 160, 160a of FIGS. 11a and 11d (as well as tubings 1560 and 1660 of FIGS. 11g and 11h) provide a distinct advantage over the prior art in that a jumble of wires and tubes exiting instrument 100 is avoided. In addition, by providing a clip such as shown in FIGS. 11e and 11f, issues regarding the sterile field can be avoided, as the clip can be positioned at a point on operating room table where sufficient length of tubing for flexibility is provided, and that tubing will all be maintained in the sterile field, while all tubing beyond the clip will be assumed to be located out of the sterile field.

Figure 12A:
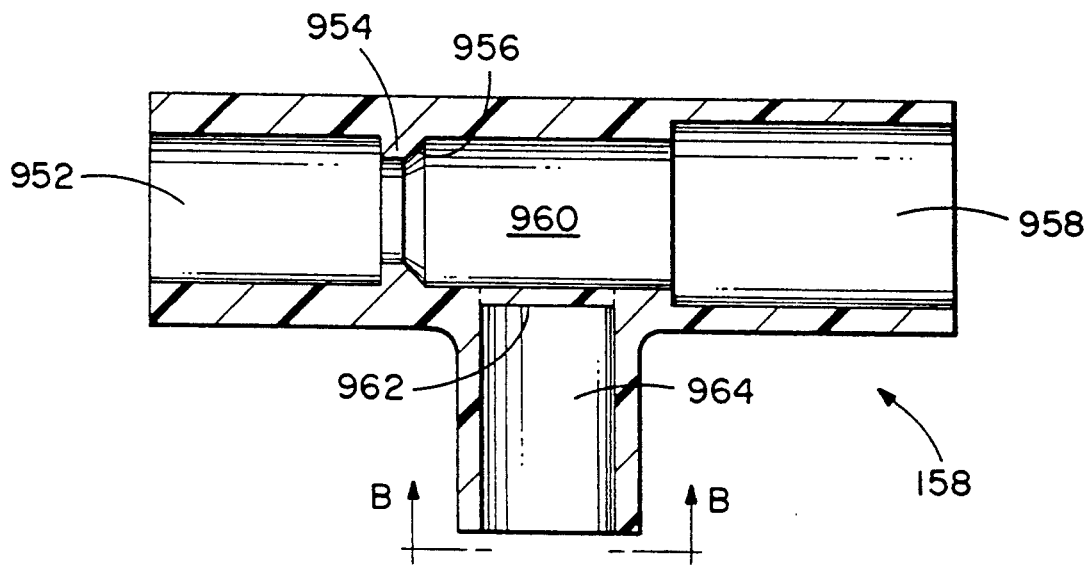
FIGS. 12a–12e show details of the T-ball valve for use in providing irrigation fluids to the instrument of the invention.
Figure 12B:
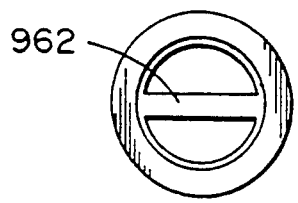
Figure 12C:
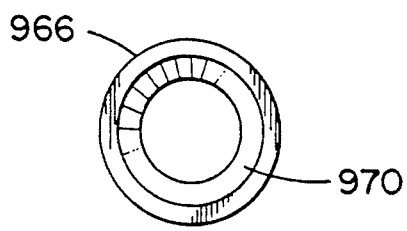
Figure 12D:
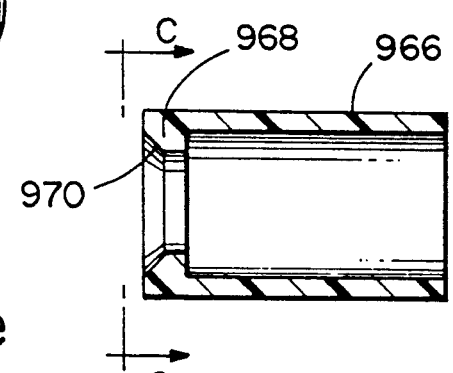
Figure 12E:
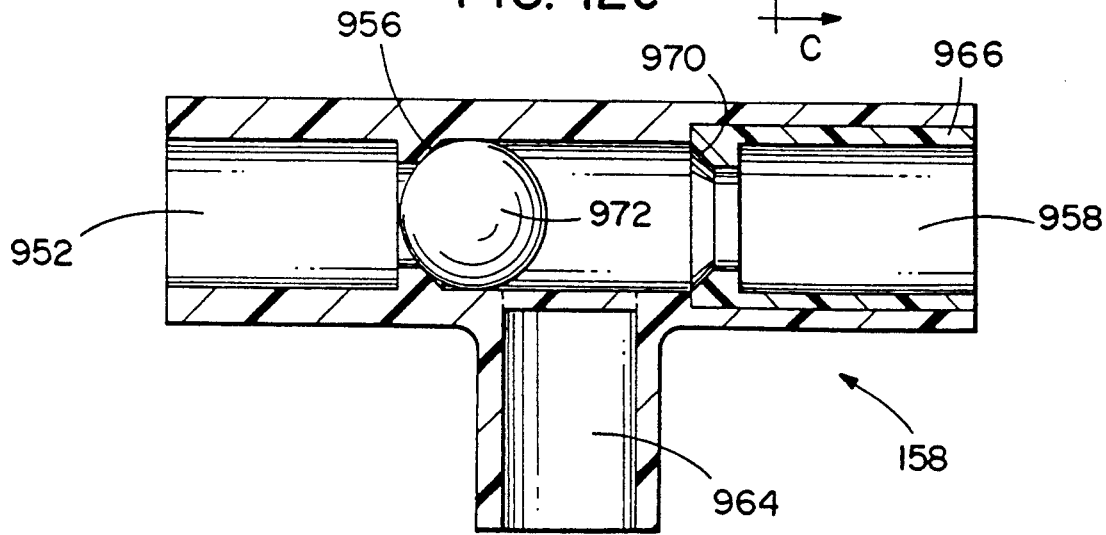

As mentioned above in reference to FIG. 1a, and according to a further aspect of the invention, a T-ball valve is provided to couple two sources of irrigation fluid to a single irrigation supply tube. FIGS. 12a–12e show details of such a T-ball valve, and it can be seen that the T-ball valve 158 preferably comprises three fluid chambers 952, 958, and 964 and a ball chamber 960. Ball chamber 960 is separated from fluid chamber 952 by a shoulder 954 having an inclined edge 956 facing ball chamber 960 so that the ball 972 will not enter fluid chamber 952 but may sealingly seat against the inclined edge 956 of shoulder 954. Ball chamber 960 is separated from the fluid chamber 964 by a narrow connecting piece 962 which is shown clearly in FIG. 12b (which is a cross section along line B—B of FIG. 12a) and is provided so that the ball will not enter chamber 964. Of course, other means such as bumps or protrusions (i.e., partial connecting pieces 962) can be used for this same purpose. In the preferred embodiment, fluid chamber 958 is dimensioned to be larger than fluid chamber 952 so that it can receive an insert 966 (FIG. 12d) after the ball 972 is placed in the ball chamber 960. The insert 966 has inner dimensions similar to the fluid chamber 952 with a shoulder 968 having an inclined edge 970 facing ball chamber 960 so that the ball 972 will not enter fluid chamber 958 but will sealingly seat against inclined edge 970. As shown in FIG. 12e, ball 972 is seated against inclined edge 956 thereby sealing off fluid chamber 952 so that fluid from chamber 958 may enter chamber 964 without entering chamber 952. It will be appreciated that when ball 972 is in its opposite position against inclined edge 970, fluid from chamber 952 may enter chamber 964 without entering chamber 958.

Referring back to FIG. 1a, it will be appreciated that when the irrigation fluid supply 156 is opened to enter T-ball valve 158, the ball 972 in the valve will seat against inclined edge 970 sealing the fluid chamber 958 so that fluid from fluid source 156 does not enter the tube leading to fluid source 154. When fluid in fluid source 156 is exhausted and fluid source 154 is opened, the ball 972 will be forced by the fluid entering chamber 958 to seat against inclined edge 956 thereby sealing chamber 952 and preventing fluid from fluid source 154 from entering fluid source 156.

As mentioned in reference to FIG. 1b, the shell 102 of instrument 100 includes trigger switches operating valves for suction and irrigation. One type of valve was shown and discussed in reference to FIGS. 3a and 3b. FIGS. 13a-13c and 13d-13e show two other types of valve arrangement which can be used with alternate embodiments of fluid chamber as will be discussed in detail below with reference to FIG. 14a and 14b.

Figure 13A:
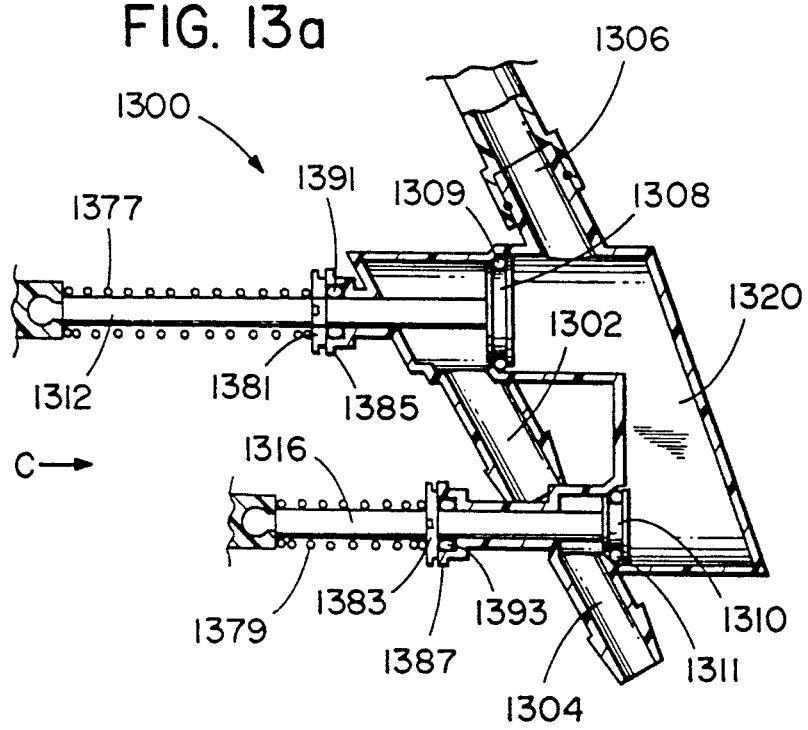
FIGS. 13a and 13b show an alternate embodiment of the fluid port and valve portion of the invention where a single suction/irrigation port is in fluid communication with the fluid chamber, and poppet valves are in respective first and second positions to respectively cause suction and irrigation.
Figure 13C:
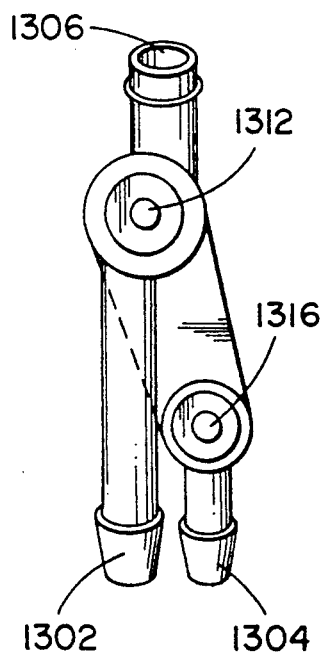
FIG. 13c is a view of FIG. 13a looking in the direction of arrow C thereof.

Referring now to FIGS. 13a and 13c, a valve assembly 1300 includes a suction conduit 1302 which is coupled to a vacuum source (not shown), an irrigation conduit 1304 which is coupled to a source of irrigation fluid (not shown), and single port 1306 connected to the fluid chamber 1414a (FIG. 14a), and two poppets having disks 1308 and 1310, and stems or rods 1312 and 1316. Valve disks 1308 and 1310 are preferably provided with O-ring seals 1309, 1311 around their outer surfaces. Valve disk 1308 is shown in the path Which connects the suction conduit 1302 with port 1306, and valve disk 1310 is shown in the path which connects the irrigation conduit 1304 with port 1306 via connecting space or chamber 1320. The poppet valve disks 1308 and 1310 are operable by poppet valve stems or rods 1316 and 1312 which are biased by springs 1377 and 1379 in the triggers (see FIG. 1b). Thus, the suction trigger 104 (FIG. 1b) is attached to stem 1312 to operate poppet valve disk 1308, and irrigation trigger 106 is attached to poppet stem 1316 to operate poppet valve disk 1310. The valve assembly 1300 includes holes 1381, 1383 and chambers 1385, 1387 housing O-rings 1391, 1393 through which the stems 1312, 1316 extend, to prevent leakage out through the trigger mechanism.

Figure 13B:
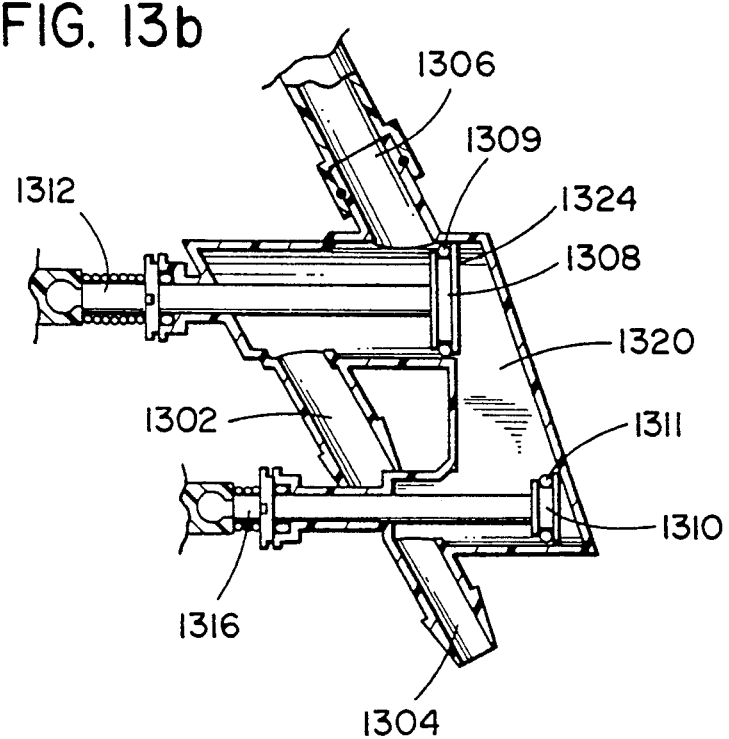

By comparing FIGS. 13a and 13b, it is seen that irrigation valve disk 1310 is movable from a first position shown in FIG. 13a where irrigation conduit 1304 is sealed from the fluid chamber 1320 (and hence from fluid port 1306) to a second position shown in FIG. 13b. In FIG. 13b, the irrigation fluid passes from inlet 1304 to chamber 1320 and, if valve seal 1308 is in the closed position as it is in FIG. 13a, up into port 1306. Likewise, suction valve disk 1308 is movable from a first position shown in FIG. 13a where the suction conduit 1302 is sealed from the port 1306 to a second position shown in FIG. 13b where the suction conduit 1302 communicates with the port 1306, and chamber 1320 is sealed off from the port 1306. It is noteworthy that when the suction trigger is fully depressed, the chamber is sealed off so that no suctioned material enters chamber 1320 to be later mixed with irrigation fluid and/or clog the valve. If desired, a seat 1324 (shown in phantom) may be provided as a back stop for disk 1308 in order to provide a more secure closure against the possibility of suctioned materials entering chamber 1320. It should be appreciated, that with the valve assembly arrangement of FIGS. 13a-13c, that if it is desired to clean the chamber 1320 and/or suction conduit 1302, the triggers for the suction and irrigation may be pressed at the same time, with the suction valve only partially opened. This will cause a flow from irrigation conduit 1304 past valve disk 1310 and into chamber 1320, and then around and past valve 1308 and down suction conduit 1302.

Figure 14A:
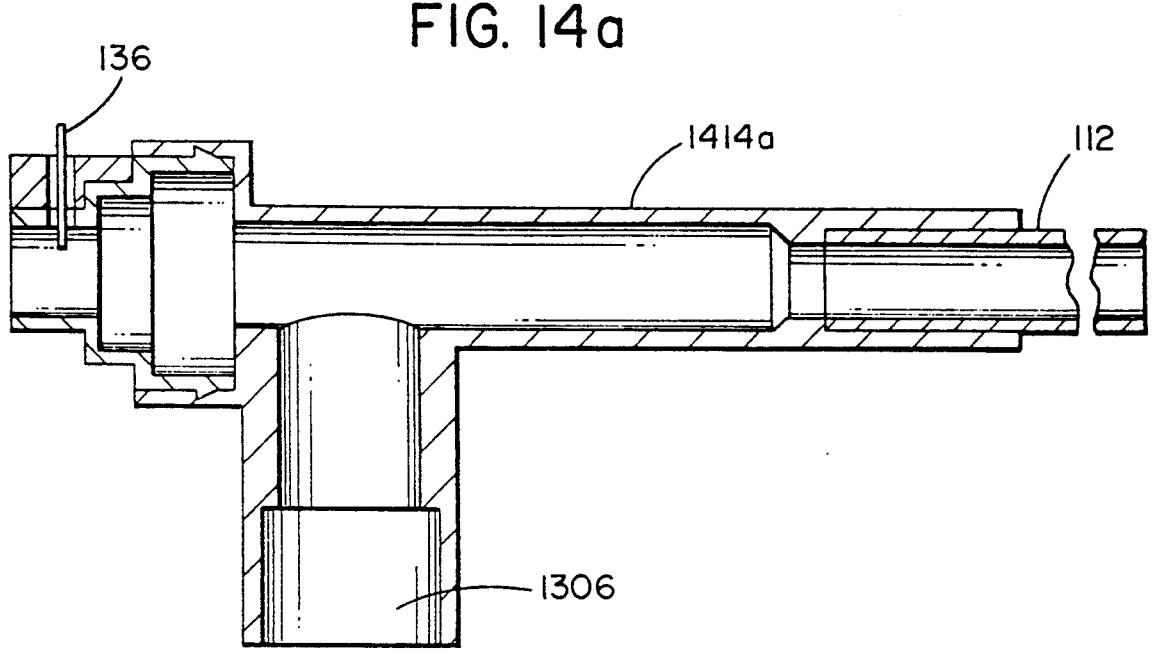
FIGS. 14a and 14b are cross sections of alternate fluid chambers for use with the fluid port and valve portions of FIGS. 13a and 13d respectively.

The fluid chamber 1414a of FIG. 14a, which in most respects is the same as fluid chamber 114 discussed above with reference to FIGS. 1b, and 4a-4b, is provided for the valve assembly 1300 of FIGS. 13a-13c. As seen in FIG. 14a, fluid chamber 1414a has a single combined suction-irrigation port 1306. The provision of a fluid chamber with a single port for both suction and cautery permits the fluid chamber, and thus the entire instrument to be made smaller.

Figure 13D:
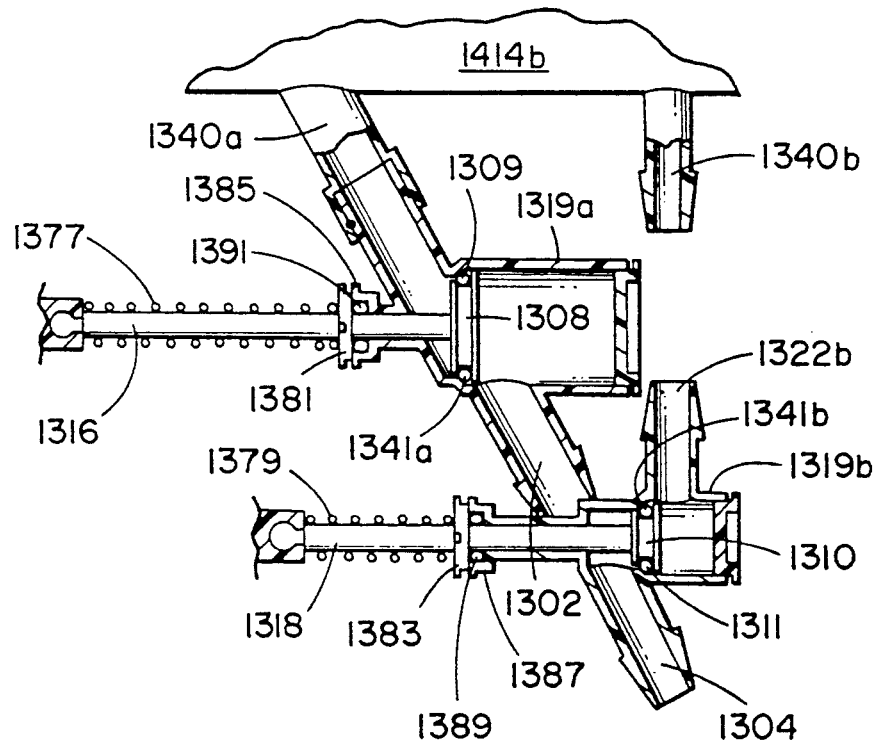
FIGS. 13d and 13e show a second alternate embodiment of the fluid port and valve portion of the invention where poppet valves are used in conjunction with separate suction and irrigation ports in fluid communication with the fluid chamber.
Figure 13E:
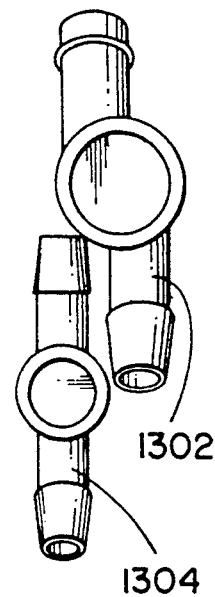

FIGS. 13d and 13e show yet another embodiment of a poppet valve assembly which may be used with yet another embodiment of the fluid chamber 1414b of FIG. 14b which will be discussed in below. The embodiment of FIGS. 13d and 13e is similar to the arrangement of FIGS. 13a-13c, except that in this embodiment, there are two ports 1340a and 1340b leading to fluid chamber 1414b, and no common chamber 1320. In particular, a suction poppet valve, having a disk 1308 and a stem 1316 is provided in the path of suction conduit 1302, 1332a. Suction conduit 1304 is coupled to a vacuum source (not shown), and the conduit outlet 1332a is coupled via fluid chamber port 1340a to the fluid chamber 1414b. Poppet valve disk 1308 is biased in a closed position by spring 1377 which is connected to trigger 104 (see FIG. 1b), and the disk 1308 is provided with an O-ring 1309 to seat in the normally closed position against a seat 1341a at one end of the valve chamber 1319a. Valve chamber 1319a is provided to permit the travel of disk 1308 out of the suction conduit path 1322a, 1302.

The irrigation system in the poppet valve assembly of FIGS. 13d and 13e is similar to the suction system. An irrigation valve, having a disk 1310 and a stem 1318 is provided in the path of irrigation conduit 1304, 1322b. Irrigation conduit is coupled to an irrigation source (not shown), and the irrigation outlet 1322b is coupled via fluid chamber port 1340b to the fluid chamber 1414b. Poppet valve disk 1310 is biased in a closed position by spring 1379 which is connected to trigger 106 (see FIG. 1b), and the disk 1310 is provided with an O-ring 1311 to seat in the normally closed position against a seat 1341b at one end of the valve chamber 1319b. Valve chamber 1319b is provided to permit the travel of disk 1310 out of the irrigation conduit path 1322b, 1304.

As seen in FIGS. 13d and 13e, the suction port 1340a is angled relative to fluid chamber 1414b, while the irrigation is not so angled. The angle of suction port 1340a is purposely provided so that the flow through the port 1340a, the outlet 1332a, and conduit 1304 is a straight path. In this manner, clogging of the port or conduit is best avoided. Also, the manufacturing process will be considerably easier. On the other hand, because the irrigation path will not clog, the tortuousness of the path is not of particular concern. Thus, the irrigation path is chosen simply to reduce the size of the apparatus.

Figure 14B:
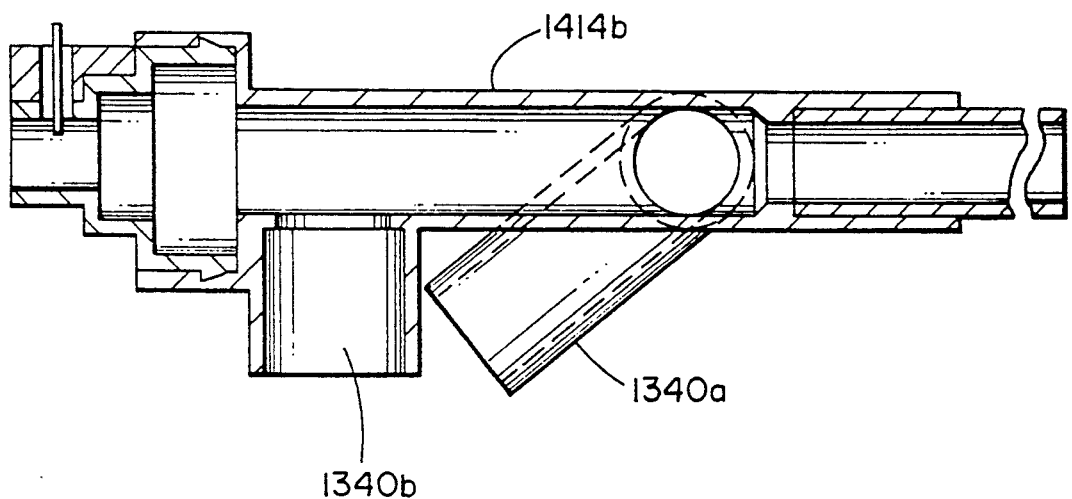

FIG. 14b shows another fluid chamber 1414b which is in most respects the same as fluid chamber 114 discussed above, but where irrigation conduit port 1340b enters from the bottom and suction port 1340a enters in an angled manner from the side. The angled suction port configuration permits an offset between fluid conduits which eliminates suction flow path tortuousness, and provides a compact assembly.

There have been described and illustrated herein several embodiments of an endoscopic suction-irrigation instrument with electrosurgical capabilities, probes for use with the instrument, valves, circuits, switches, and connectors. While particular embodiments of the invention have been described, it is not intended that the invention be limited thereto, as it is intended that the invention be as broad in scope as the art will allow and that the specification be read likewise. Thus, while a particular pistol shape for the instrument shell has been disclosed, it will be appreciated that many other shapes could be used with similar results. Also, while particular configurations of triggers and switches have been shown, other actuating means may easily be adopted for use with the invention. Moreover, while the fluid chamber has been described in several embodiments as including a locking pin, an electrical contact and a slit valve, it will be appreciated that the locking pin and electrical contact could be provided outside the fluid chamber and other types of valves could be substituted for the slit valve, even though the slit valve is particularly advantageous. Further, while several different probes, each with different features have been disclosed, it will be appreciated that the features of different probes may be combined in many different ways to provide even more types of probes for use with the invention. Likewise, while particular endoscopic and laparoscopic tools were shown as modified for insertion into the suction/irrigation instrument of the invention so as to effect cautery, it will be appreciated that the instruments need not be modified, and that numerous other tools could be used in conjunction with the suction/irrigation instrument of the invention, with or without modification as desired. Further yet, while it will be appreciated that the preferred materials for the tubing of the disclosed instrument is Kraton (a thermoplastic elastomer), and that the preferred materials for the fluid chamber, shell, triggers, etc. is ABS (acrylonytrile butadiene styrene), other materials could be utilized. It will therefore be appreciated by those skilled in the art that yet other modifications could be made to the provided invention without deviating from its spirit and scope as so claimed.

What is claimed is:

1. A pinch valve for a flexible conduit having a wall with an outer surface of a first diameter and an inner surface of a second diameter, said pinch valve comprising:
    a) a first arcuate rigid means having an inner arcuate surface of a third diameter substantially equal to said first diameter wherein said inner arcuate surface receives said outer surface of first diameter of said flexible conduit;
    b) a second arcuate rigid means having an outer arcuate surface of a fourth diameter at least as small as said second diameter, and said flexible conduit is located between said first and second arcuate rigid means;
    c) actuator means coupled to one of said first and second arcuate rigid means, said actuator means for moving said one of said first and second arcuate rigid means relative to another of said first and second arcuate rigid means from a first position to collapse and pinch said flexible conduit therebetween to a second position where said flexible conduit is not collapsed and pinched;
    d) biasing means for urging said first and second conduit rigid means towards each other so as to collapse and pinch said flexible conduit in a default position; and
    e) finger activated trigger means coupled to said biasing means and to said actuator means, and substantially coaxial with said actuator means.

2. A pinch valve according to claim 1, wherein:
said wall is sufficiently thick with said first diameter being sufficiently larger than said second diameter such that said wall of said flexible conduit is compressed after said conduit is completely collapsed.

3. A pinch valve according to claim 1, wherein:
said second arcuate rigid means is fixed, and said actuator means moves said first arcuate rigid means toward said second arcuate rigid means.

4. A pinch valve according to claim 1, wherein:
said wall is sufficiently thick with said first diameter biasing means is sufficiently strong such that said wall of said flexible conduit is compressed by being squeezed between said first arcuate rigid means and said second arcuate rigid means after said conduit is completely collapsed.

5. A pinch valve according to claim 4, wherein:
said second arcuate rigid means is fixed, and said actuator means moves said first arcuate rigid means toward said second arcuate rigid means.

6. A pinch valve according to claim 1, wherein:
said biasing means comprises a spring.

7. A pinch valve according to claim 1,
wherein:
said biasing means comprises a spring, and
said first arcuate rigid means further comprises a flat inner surface portion, and said second arcuate rigid means further comprises a flat outer surface portion, said flat inner surface portion being displaced from said flat outer surface portion, and said spring is located between said flat inner surface portion and said flat outer surface portion.

8. A pinch valve according to claim 7, wherein:
said spring biases said flat inner surface portion away from said flat outer surface portion.

9. A pinch valve according to claim 8, wherein:
said wall is sufficiently thick with said first diameter being sufficiently larger than said second diameter, and said spring means is sufficiently strong such that said wall of said flexible conduit is compressed by being squeezed between said first arcuate rigid means and said second arcuate rigid means after said conduit is completely collapsed.

10. A pinch valve for a flexible conduit having a wall with an outer surface of a known first diameter and an inner surface of a known second diameter, said pinch valve comprising:
    a) a first arcuate rigid means having an arcuate surface of a third diameter substantially equal to said first known diameter wherein said inner arcuate surface receives said outer surface of first diameter of said flexible conduit;
    b) a fixed second arcuate rigid means having an outer arcuate surface of a fourth diameter at least as small as said second known diameter, and said flexible conduit is located between said first and second arcuate rigid means;
    c) actuator means coupled to said first arcuate rigid means, said actuator means for moving said first arcuate rigid means relative to said second arcuate rigid means from a first position to collapse and pinch said flexible conduit therebetween to a second position where said flexible conduit is not collapsed and pinched;
    d) biasing means for urging said first and second arcuate rigid means towards each other so as to collapse and pinch said flexible conduit in a default position; and
    e) finger activated trigger means coupled to said biasing means and to said actuator means, and substantially coaxial with said actuator means.

11. A pinch valve according to claim 10, wherein:
said wall is sufficiently thick with said known first diameter being sufficiently larger than said second diameter, and said biasing means is sufficiently strong such that said wall of said flexible conduit is compressed by being squeezed between said first arcuate rigid means and said second arcuate rigid means after said conduit is completely collapsed.

12. A pinch valve according to claim 11, wherein:
said biasing means comprises a spring.

13. A pinch valve according to claim 10, wherein:
said biasing means comprises a spring, and
said first arcuate rigid means further comprises a flat inner surface portion, and said second arcuate rigid means further comprises a flat outer surface portion, said flat inner surface portion being displaced from said flat outer surface portion, and said spring is located between said flat inner surface portion and said flat outer surface portion.

14. A pinch valve according to claim 13, wherein:
said spring biases said flat inner surface portion away from said flat outer surface portion.

15. A pinch valve for a flexible conduit having a wall within an outer surface of a first diameter and an inner surface of a second diameter, said pinch valve comprising:
   a) a first arcuate rigid means having an inner arcuate surface of a third diameter substantially equal to said first diameter wherein said inner arcuate surface receives said outer surface of first diameter of said flexible conduit;
   b) a second arcuate rigid means having an outer arcuate surface of a fourth diameter at least as small as said second diameter, and said flexible conduit is located between said first and second arcuate rigid means;
   c) actuator means coupled to one of said first and second arcuate rigid means, said actuator means for moving said one of said first and second arcuate rigid means relative to another of said first and second arcuate rigid means from a first position to collapse and pinch said flexible conduit therebetween to a second position where said flexible conduit is not collapsed and pinched;
   d) biasing means for urging said first and second arcuate rigid means towards each other so as to collapse and pinch said flexible conduit in a default position; and
   e) finger activated trigger means coupled to said biasing means and to said actuator means, and substantially coaxial with said actuator means, wherein
said wall is sufficiently thick with said first diameter being sufficiently larger than said second diameter, and said spring means is sufficiently strong such that said wall of said flexible conduit is substantially compressed by being squeezed between said first arcuate rigid means and said second arcuate rigid means after said conduit is completely collapsed.

16. A pinch valve according to claim 15, wherein:
said second arcuate rigid means is fixed, and said actuator means moves said first arcuate rigid means toward said second arcuate rigid means.

17. A pinch valve according to claim 15, wherein:
said biasing means comprises a spring, and
said first arcuate rigid means further comprises a flat inner surface portion, and said second arcuate rigid means further comprises a flat outer surface portion, said flat inner surface portion being displaced from said flat outer surface portion, and said spring is located between said flat inner surface portion and said flat outer surface portion.

18. A pinch valve according to claim 17, wherein:
said spring biases said flat inner surface portion away from said flat outer surface portion.

* * * * *